United States Patent [19]

Kubota et al.

[11] 4,351,915
[45] Sep. 28, 1982

[54] 2,2,6,6-TETRAMETHYL-4-PIPERIDYL SPIRO ALIPHATIC ETHERS AS STABILIZERS FOR SYNTHETIC POLYMERS

[75] Inventors: Naohiro Kubota, Ageo; Toshihiro Shibata, Omiya; Kazuo Sugibuchi, Tokyo; Motonubu Minagawa, Koshigaya, all of Japan

[73] Assignee: Adeka Argus Chemical Co., Ltd., Urawa, Japan

[21] Appl. No.: 267,138

[22] Filed: May 26, 1981

[30] Foreign Application Priority Data

May 30, 1980 [JP] Japan .................. 55-72875

[51] Int. Cl.³ ............... C07D 491/10; C07F 5/04; C07F 7/10; C07F 9/65; C08K 5/34; C08K 5/46; C08K 5/52; C08K 5/53; C08K 5/54; C08K 5/55; C08G 18/32; C08G 18/38; C08G 63/68; C08G 65/40

[52] U.S. Cl. .................... 524/103; 524/99; 524/101; 524/102; 524/84; 528/7; 528/30; 528/38; 528/40; 528/72; 528/73; 528/168; 528/183; 528/184; 528/188; 528/287; 528/289; 544/223; 546/13; 546/14; 546/19

[58] Field of Search ........... 260/45.8 NP, 45.8 NT; 546/13, 14, 19; 544/223; 528/72, 73, 168, 183, 184, 188, 30, 38, 40, 7, 287, 289

[56] References Cited

U.S. PATENT DOCUMENTS

| | | | |
|---|---|---|---|
| 4,096,114 | 6/1978 | Minagawa et al. | 546/19 |
| 4,105,625 | 8/1978 | Minagawa et al. | 546/19 |
| 4,105,626 | 8/1978 | Brunetti et al. | 546/19 |
| 4,115,476 | 9/1978 | Minagawa et al. | 546/19 |
| 4,136,081 | 1/1979 | Minagawa et al. | 546/19 |
| 4,173,599 | 11/1979 | Minagawa et al. | 546/19 |
| 4,177,186 | 12/1979 | Rody et al. | 546/14 |
| 4,212,974 | 7/1980 | Murayama et al. | 546/19 |
| 4,222,931 | 12/1980 | Minagawa et al. | 546/19 |
| 4,237,294 | 12/1980 | Soma et al. | 546/19 |
| 4,250,312 | 2/1981 | Nakahara et al. | 546/19 |
| 4,265,803 | 5/1981 | Soma et al. | 546/19 |
| 4,312,804 | 1/1982 | Minagawa et al. | 260/45.8 NP |

Primary Examiner—V. P. Hoke

[57] ABSTRACT 2,2,6,6-Tetramethyl-4-piperidyl spiro aliphatic ethers which are useful as stabilizers for organic polymeric materials, and have the general formula are disclosed:

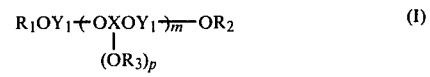

wherein:
$Y_1$ is

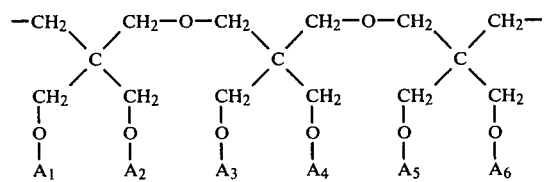

$A_1$, $A_2$, $A_3$, $A_4$, $A_5$, and $A_6$ are groups which are defined in the specification, at least one pair of $A_1$ and $A_2$; $A_3$ and $A_4$; and $A_5$ and $A_6$ being taken together to form the group

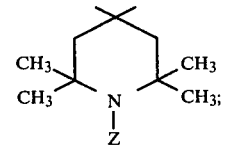

the groups $R_1$, $R_2$, $R_3$ and Z as well as X, p, and m being as defined in the specification.

43 Claims, No Drawings

2,2,6,6-TETRAMETHYL-4-PIPERIDYL SPIRO ALIPHATIC ETHERS AS STABILIZERS FOR SYNTHETIC POLYMERS

Minagawa, Kubota and Shibata, U.S. Pat. No. 4,128,608, patented Dec. 5, 1978, provide 2,2,6,6-tetramethyl-4-piperidyl spiro aliphatic ethers useful as stabilizers for organic polymeric materials, and having the general formula:

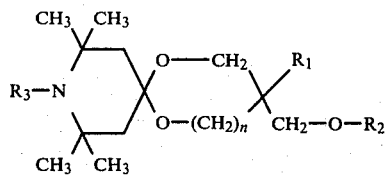

wherein:

$R_1$ is selected from the group consisting of hydrogen; lower alkyl and lower hydroxyalkyl having one or two carbon atoms;

$R_2$ is

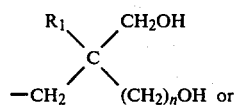

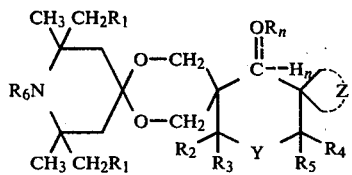

$R_3$ is selected from the group consisting of hydrogen and O.; and n is 0 to 1.

Minagawa, Kubota and Shibata, U.S. Pat. No. 4,173,599, patented Nov. 6, 1979, provide 2,2,6,6-tetraalkyl-4-piperidyl ketones and ketals useful as stabilizers for organic polymeric materials, and having the general formula:

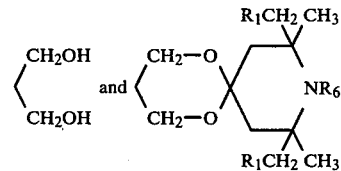

wherein:

n are each 0 or 1 and are each the same;

R is selected from the group consisting of hydrogen; alkyl having from one to about eighteen carbon atoms; and acyl

R' being alkyl having from one to about eighteen carbon atoms;

$R_1$, $R_2$, $R_3$, $R_4$ and $R_5$ are selected from the group consisting of hydrogen and alkyl having from one to about eighteen carbon atoms;

$R_6$ is selected from the group consisting of hydrogen and O.;

Y is selected from the group consisting of a carbon-to-carbon bond—, oxy —O—; alkylene having from one to about three carbon atoms, and alkyl-substituted alkylene, the alkylene having from one to about three carbon atoms, the alkyl having from one to about six carbon atoms; and Z is selected from the group consisting of:

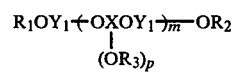

In accordance with the instant invention, 2,2,6,6-tetramethyl-4-piperidyl spiro aliphatic ethers are provided, useful as stabilizers for organic polymeric material, and having the general formula:

$$R_1OY_1+OXOY_1\xrightarrow{}_{m}OR_2 \qquad (I)$$
$$(OR_3)_p$$

wherein:
$Y_1$ is

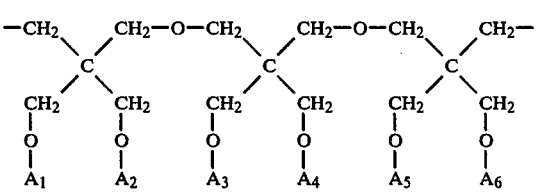

$A_1$, $A_2$, $A_3$, $A_4$, $A_5$, and $A_6$ each are selected from the group consisting of hydrogen; alkyl and hydroxyalkyl having from one to about eighteen carbon atoms; cycloalkyl having from three to about eight carbon atoms; aryl having from about six to about eighteen carbon atoms; acyl having from one to about eighteen carbon atoms

wherein $R_4$ is selected from the group consisting of aliphatic having from one to about eighteen carbon atoms; cycloaliphatic having from three to about eight carbon atoms; heterocyclic having from six to about eighteen carbon atoms; and aromatic having from six to about eighteen carbon atoms; carbamoyl

wherein $R_5$ is selected from the group consisting of aliphatic having from one to about eighteen carbon atoms; cycloaliphatic having from three to about eight carbon atoms; heterocyclic having from six to about eighteen carbon atoms; and aromatic having from six to about eighteen carbon atoms;

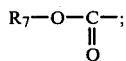

and monovalent oxyacid groups; at least one pair of $A_1$ and $A_2$; $A_3$ and $A_4$; and $A_5$ and $A_6$ being taken together to form the group:

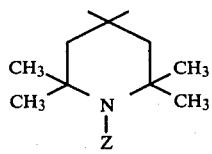

wherein:

Z is selected from the group consisting of hydrogen; oxyl O.; alkyl and hydroxyalkyl having from one to about twenty carbon atoms; and aryl and hydroxyaryl having from six to about twenty carbon atoms;

X is selected from the group consisting of alkylene having from one to about eighteen carbon atoms; cycloalkylene having from three to about eight carbon atoms; arylene having from about six to about eighteen carbon atoms; polyacyl

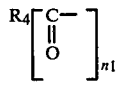

wherein $R_4$ is as above and $n_1$ is a number from 2 to 4; polycarbamoyl

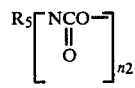

wherein $R_5$ is as above and $n_2$ is a number from 2 to 4;

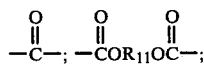

and di- and trivalent oxyacid groups;

$R_1$ and $R_2$ each are selected from the group consisting of hydrogen; alkyl having from one to about eighteen carbon atoms; cycloalkyl having from three to about eight carbon atoms; aryl having from about six to about eighteen carbon atoms; carbamoyl

wherein $R_5$ is selected from the group consisting of aliphatic having from one to about eighteen carbon atoms; cycloaliphatic having from three to about eight carbon atoms; heterocyclic having from six to about eighteen carbon atoms; and aromatic having from six to about eighteen carbon atoms;

and monovalent oxyacid groups;

$R_3$ is selected from the group consisting of alkyl having from one to about eighteen carbon atoms; cycloalkyl having from three to about eight carbon atoms; aryl having from about six to about eighteen carbon atoms; and $-X-O-R_1$;

$R_7$ is selected from the group consisting of the residues of monohydric alcohols having from one to about eighteen carbon atoms and phenols having from six to about fifty carbon atoms;

$R_{11}$ is selected from the group consisting of alkylene and oxyalkylene having from two to about ten carbon atoms and from zero to about five oxyether groups; cycloalkylene having from three to about eight carbon atoms; and arylene having from six to about fifty carbon atoms; and isocyanurate;

m is a number from zero to 10; and p is zero or 1.

In formula (I), exemplary $A_1$, $A_2$, $A_3$, $A_4$, $A_5$, $A_6$, $R_1$, $R_2$ and $R_3$ and Z alkyl include methyl, ethyl, propyl, butyl, octyl, 2-ethylhexyl, isooctyl, decyl, dodecyl, tetradecyl, octadecyl; exemplary $A_1$, $A_2$, $A_3$, $A_4$, $A_5$, $A_6$, $R_1$, $R_2$ and $R_3$ cycloalkyl include cyclobutyl, cyclopropyl, cyclopentyl, cyclohexyl, cycloheptyl and cyclooctyl; exemplary $A_1$, $A_2$, $A_3$, $A_4$, $A_5$, $A_6$, $R_1$, $R_2$ and $R_3$ aryl include benzyl, phenylethyl, phenyl, toluyl, xylyl, butylphenyl and nonylphenyl.

Exemplary $A_1$, $A_2$, $A_3$, $A_4$, $A_5$, $A_6$, $R_1$, $R_2$ and $R_3$ acyl are those derived from monocarboxylic acids such as formic acid, acetic acid, propionic acid, butyric acid, pivalic acid, 2-ethylhexanoic acid, lauric acid, palmitic acid, stearic acid, acrylic acid, crotonic acid, oleic acid, acetoacetic acid, levulinic acid, pyruvic acid, ketostearic acid, aminoacetic acid, dodecylmercaptopropionic acid, 3,5-di-t-butyl-4-hydroxyphenylpropionic acid, benzoic acid, toluic acid, 4-t-butylbenzoic acid, 3,5-di-t-butyl-4-hydroxybenzoic acid, nicotinic acid, isonicotinic acid, 2,2,6,6-tetramethyl piperidine-4-carboxylic acid and 3,8,8,10,10-pentamethyl-9-aza-1,5-dioxaspiro-(5,5)-undecane-3-carboxylic acid; as well as polycarboxylic acids such as oxalic acid, malonic acid, succinic acid, glutaric acid, adipic acid, sebacic acid, dodecanedicarboxylic acid, maleic acid, phthalic acid, isophthalic acid, terephthalic acid, tricarballylic acid, butanetricarboxylic acid, butenetricarboxylic acid, trimellitic acid, butanetetracarboxylic acid, pyromellitic acid, thiophenedicarboxylic acid and furanedicarboxylic acid; and partial esters thereof.

Exemplary carbamoyl are the carbamoyl groups derived from monoisocyanates such as propylisocyanate, butylisocyanate, hexadecylisocyanate, octadecylisocyanate, phenylisocyanate, toluylisocyanate, 3,4-dichlorophenylisocyanate, nitrophenylisocyanate, tosylisocyanate and cyclohexylisocyanate; the carbamoyl groups derived from diisocyanates such as hexamethylenediisocyanate, lysinediisocyanate, phenyldiisocyanate, toluylenediisocyanate, diphenyletherdiisocyanate, xylylenediisocyanate, 3-isocyanatomethyl-3,5,5-trimethylcyclohexylisocyanate, bis(isocyanatomethyl)cyclohexane and 3-(2'-isocyanatocyclohexyl)propylisocyanate.

Exemplary monovalent groups from oxyacid are the monovalent groups derived from phosphorus-containing oxyacids such as phosphorous acid, phosphoric acid, (organic)phosphonous acid, (organic)phosphonic acid, (diorganic) phosphinous acid, and (diorganic)phosphinic acid, (organic)silicic acid, boric acid, and esters thereof.

Exemplary $R_7$ are the residues of monohydric alcohols such as methanol, ethanol, isiopropanol, butanol, pentanol, cyclohexanol, octanol, 2-ethylhexanol, isooctanol, nonanol, decanol, isodecanol, lauryl alcohol, tridecanol, myristyl alcohol, palmityl alcohol, stearyl alcohol, mono-, di- and triethyleneglycolmonoether, benzyl alcohol and phenyl ethanol; and the residues of monohydric phenols such as phenol, cresol, 4-t-butylphenol, octylphenol, nonylphenol, chlorophenol, 2,6-dimethylphenol, 2-cyclohexylphenol, 2,4-di-t-butylphenol, 2-t-butyl-4-methylphenol and dinonyl phenol.

Exemplary $R_{11}$ and X alkylene and cycloalkylene are those derived from polyhydric alcohols such as ethylene glycol, diethylene glycol, triethylene glycol, 1,2-propanediol, 1,3-propanediol, 1,2-butanediol, 1,3-butanediol, 1,4-butanediol, neopentyl glycol, thiodiethylene glycol, 1,6-hexanediol, 1,10-decanediol, 1,4-cyclohexanediol, 1,4-cyclohexanedimethanol, 1,4-phenyldimethanol, hydrogenated-Bisphenol A, glycerol, trimethylolmethane, trimethylolethane and tris-(2-hydroxyethyl)isocyanurate; exemplary $R_{11}$ arylene are those derived from polyhydric phenols such as hydroquinone, 4,4'-isopropylidenediphenol (Bisphenol A), 4,4'-cyclohexylidenediphenol, 4,4'-methylenebisphenol, 4,4'-sulfobisphenol, 2,5-di-t-butyl-hydroquinone, 2,3,6-trimethyl hydroquinone, 2-methylresorcinol, 2,2'-methylenebis-(4-methyl-6-t-butylphenol), 2,2'-methylenebis-(4-ethyl-6-t-butylphenol), 2,2'-methylenebis-[4-methyl-6-(α-methylcyclohexyl)phenol], 2,2'-n-butylidenebis-(4,6-di-methylphenol), bis-1,1-(2'-hydroxy-3',5'-di-methylphenyl)-3,5,5-trimethylhexane, 2,2'-cyclohexylidenebis-(4-ethyl-6-t-butylphenol), 2,2'-isopropylbenzylidenebis-(4-ethyl-6-t-butylphenol), 2,2'-thiobis-(4-t-butyl-6-methylphenol), 2,2'-thiobis-(4-methyl-6-t-butylphenol), 2,2'-thiobis-(4,6-di-t-butylphenol), 4,4'-methylene bis-(2-methyl-6-t-butylphenol), 4,4'-isopropylidenebis-2-phenylethylphenol), 4,4'-n-butylidenebis-(3-methyl-6-t-butylphenol), 4,4'-cyclohexylidenebis-(2-t-butylphenol), 4,4'-cyclohexylidenebis-(2-t-butylphenol), 4,4'-cyclohexylidenebis-(2-cyclohexylphenol), 4,4'-benzylidenebis-(2-t-butyl-5-methylphenol), 4,4'-oxobis-(3-methyl-6-isopropylphenol), 4,4'-thiobis-(2-methyl-6-t-butylphenol), 4,4'-thiobis-(3-methyl-6-t-butylphenol), 4,4'-sulfobis-(3-methyl-6-t-butylphenol), bis-(2-methyl-4-hydroxy-5-t-butylbenzyl)sulfide, 1,1,3-tris-(2'-methyl-4'-hydroxy-5'-t-butylphenyl) butane, 2,2-bis-(3'-t-butyl-4'-hydroxyphenyl)-4-(3'',5''-di-t-butyl-4''-hydroxyphenyl)butane and 2,2-bis-(2'-methyl-5'-t-butyl-4'-hydroxyphenyl)-4-(3'',5''-di-t-butyl-4'-hydroxyphenyl)butane.

Exemplary X alkylene include methylene, ethylene, propylene, butylene, hexamethylene and cyclohexylene; arylene include phenylene and bisphenylene; polyacyl include the polyacyl groups derived from di- and higher polycarboxylic acids, such as oxalic acid, malonic acid, succinic acid, glutaric acid, adipic acid, sebacic acid, dodecanedicarboxylic acid, eicosanedicarboxylic acid, tartaric acid, maleic acid, phthalic acid, isophthalic acid, terephthalic acid, iminodiacetic acid, thiodipropionic acid, diglycolic acid, tetrahydrophthalic acid, endomethlenetetrahydrophthalic acid, thiophenedicarboxylic acid, furanedicarboxylic acid, dicarboxyethylpiperidine, citric acid, tricarballylic acid, butanetricarboxylic acid, butenetricarboxylic acid, trimellitic acid, ethylenetetracarboxylic acid, ethanetetracarboxylic acid, 1,2,2,3-propanetetracarboxylic acid, and 1,1,2,3-propanetetracarboxylic acid.

Exemplary X polycarbamoyl include the polycarbamoyl groups derived from polyisocyanates such as hexamethylene diisocyanate, lysine diisocyanate, phenyl diisocyanate, toluylene diisocyanate, diphenylether diisocyanate, xylylene diisocyanate, 3-isocyanatomethyl-3,5,5-trimethylcyclohexyl isocyanate, bis(isocyanatomethyl) cyclohexane and 3-(2'-isocyanatocyclohexyl) propylisocyanate.

Exemplary di- and trivalent oxyacid include the groups derived from phosphorous acid, phosphoric acid, (organic) phosphonous acid, (organic)phosphonic acid, boric acid, (organic) silicic acid and dimers thereof, joined by polyhydric alcohol or phenol.

Exemplary Z alkyl, hydroxyalkyl, aryl and hydroxyaryl include methyl, ethyl, butyl, octyl, benzyl, phenylethyl, 2-hydroxyethyl, 2-hydroxypropyl, 2-hydroxybutyl, 2-phenyl-2-hydroxyethyl, 2-acetoxyethyl, 2-octyloyloxyethyl, 2-[3'-(3'',5''-di-t-butyl-4''-hydroxyphenyl)propanoyloxy] ethyl and benzoyloxyethyl.

Typical compounds having the formula (I) are shown below:

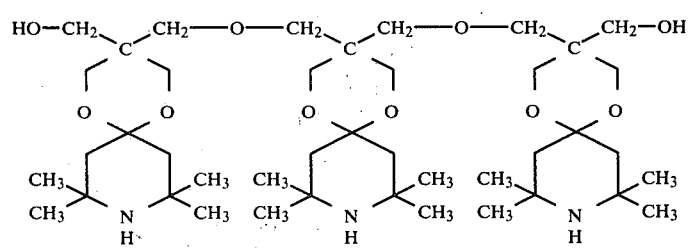

1.

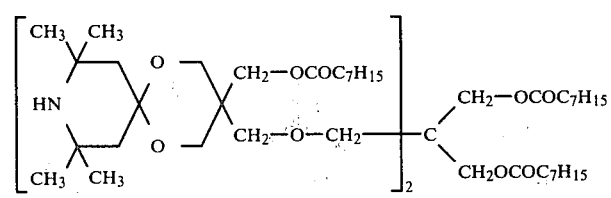

2.

3.
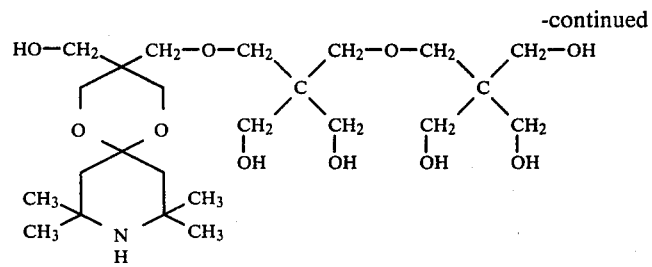
4.
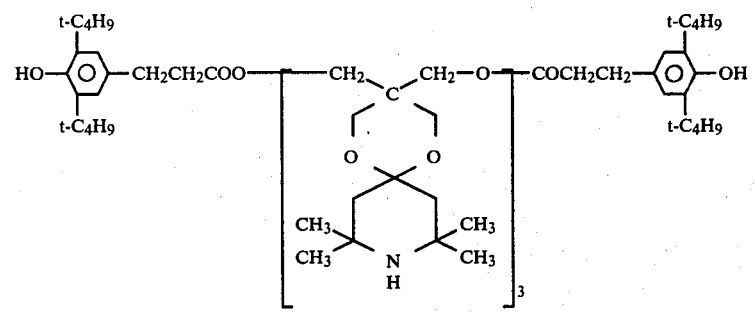
5.
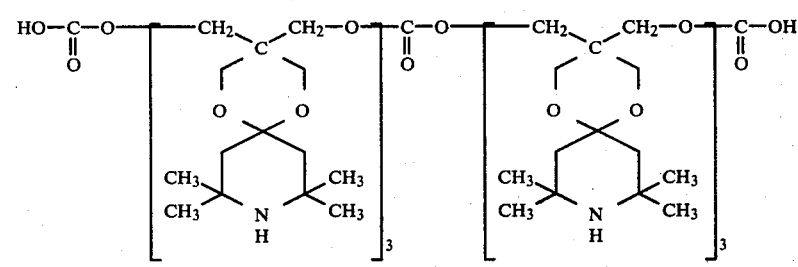
6.
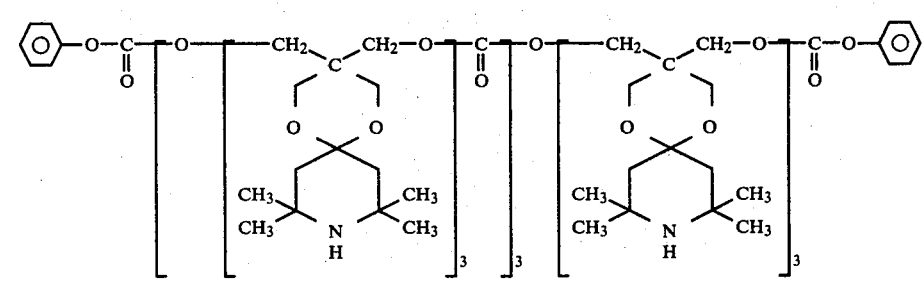
7.
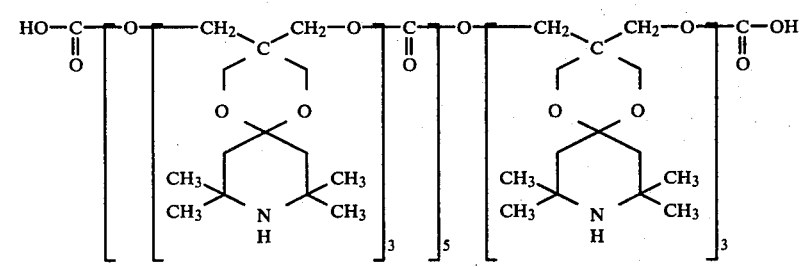
8.
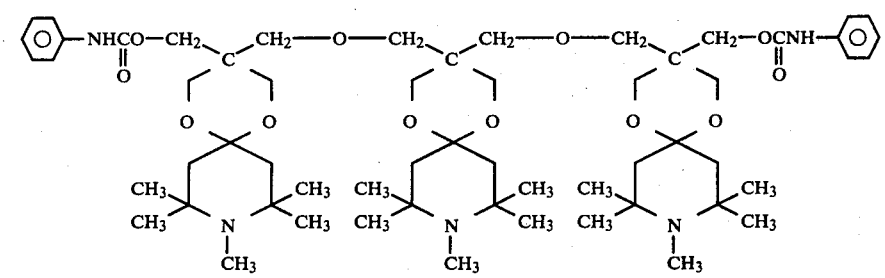

-continued
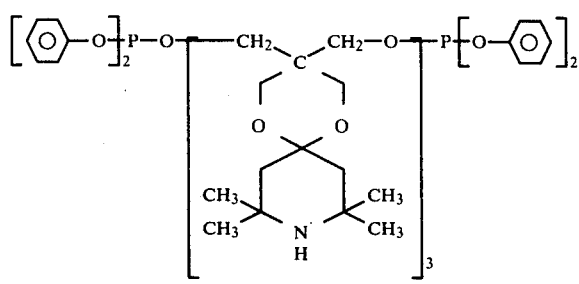 9.
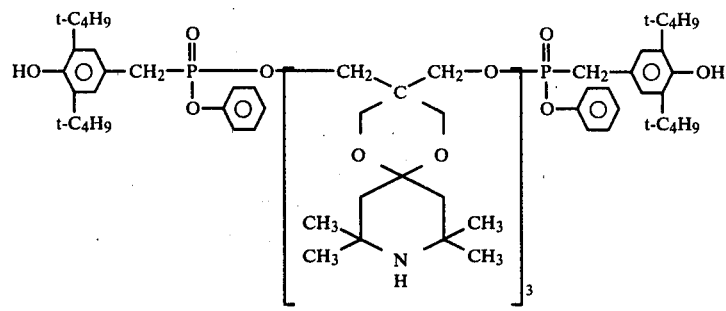 10.
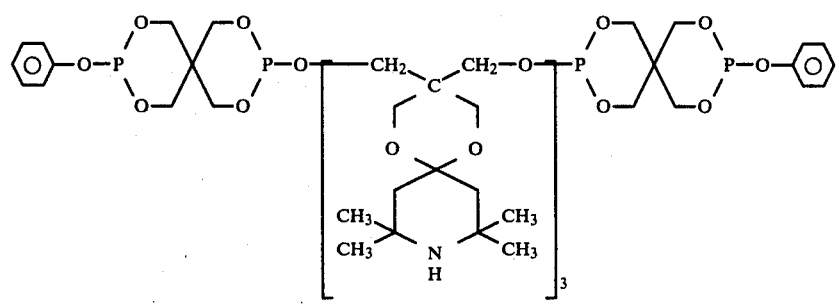 11.
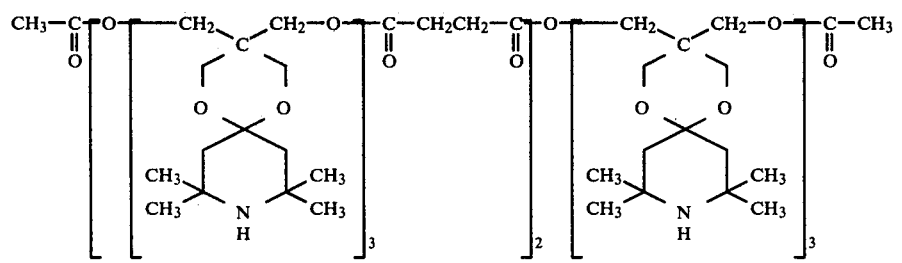 12.
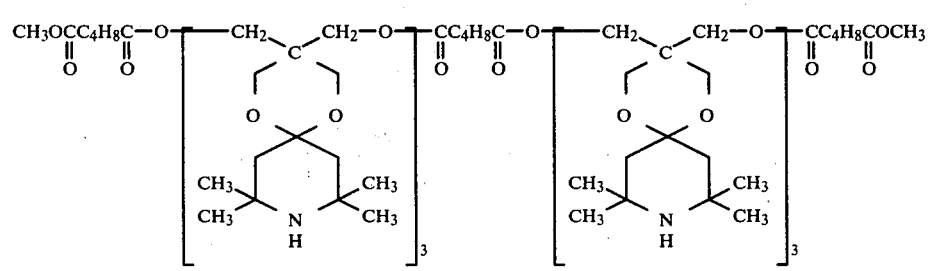 13.

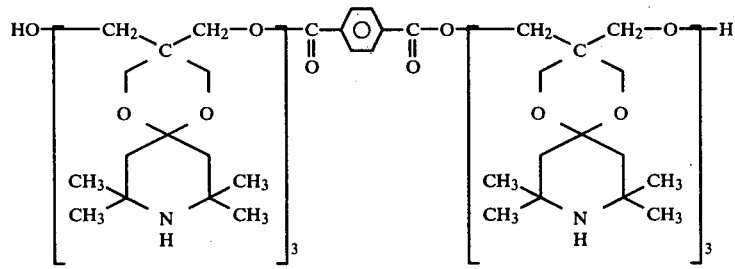
14.
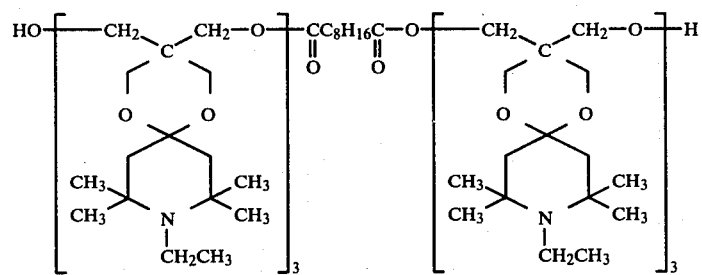
15.
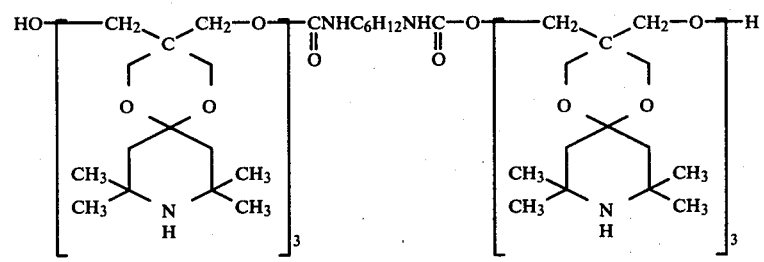
16.
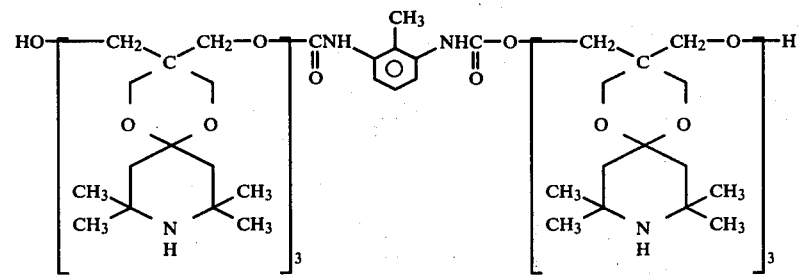
17.
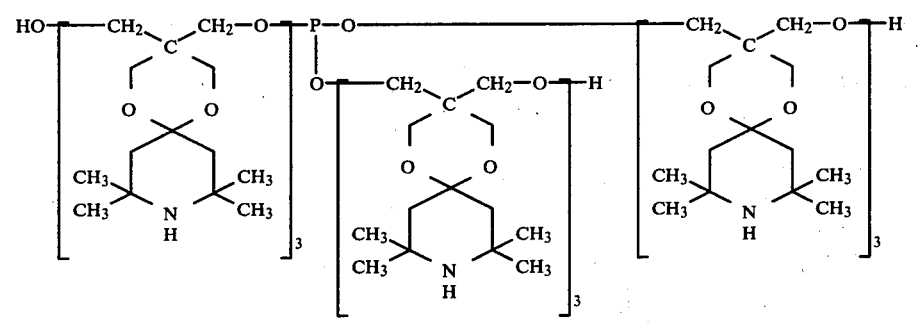
18.

-continued
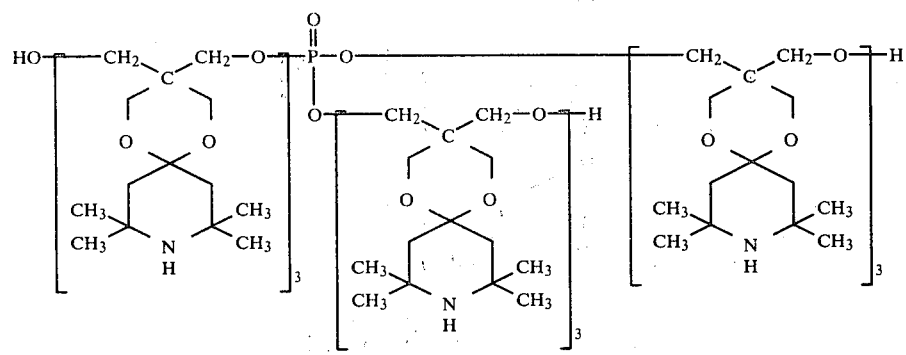
19.
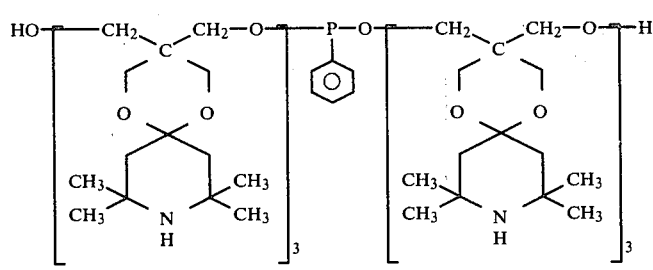
20.
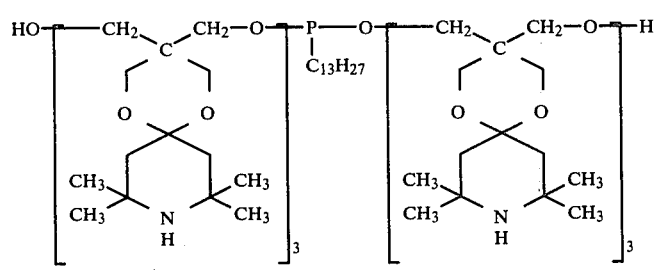
21.
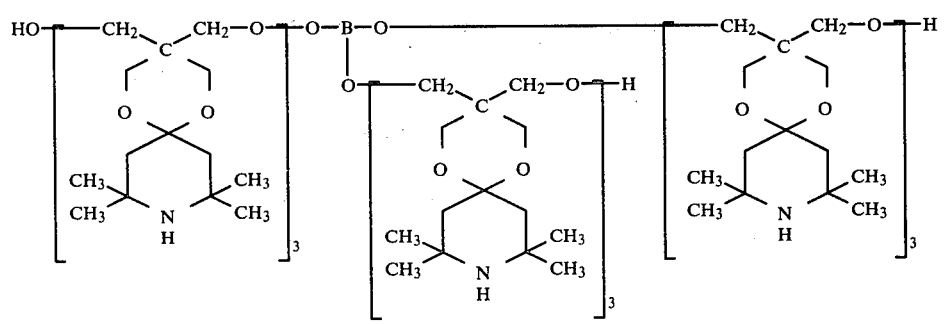
22.
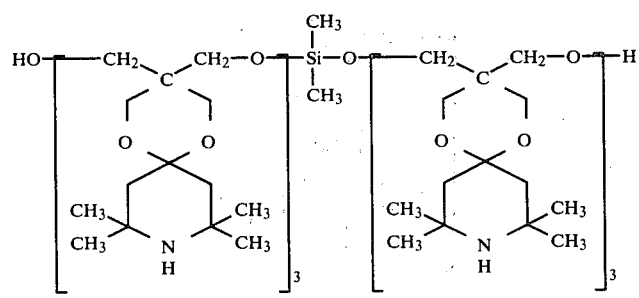
23.

-continued
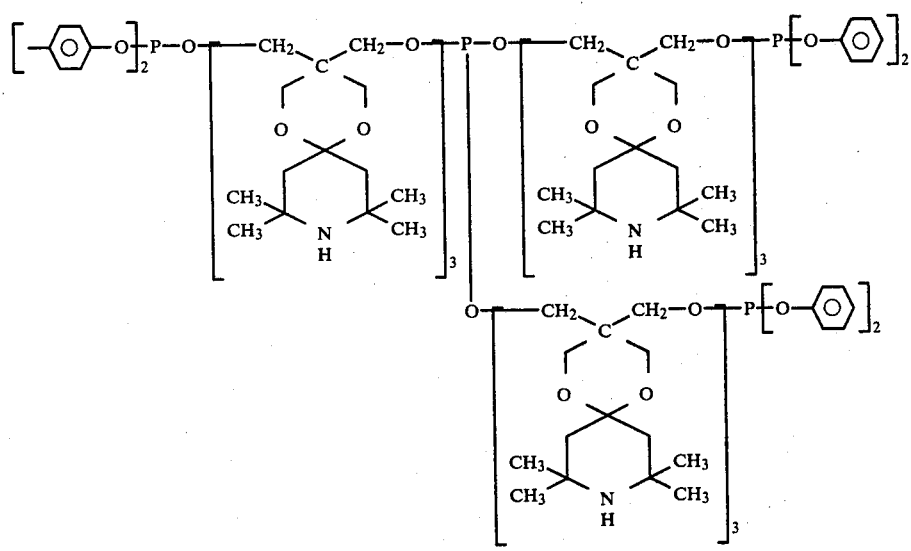
24.
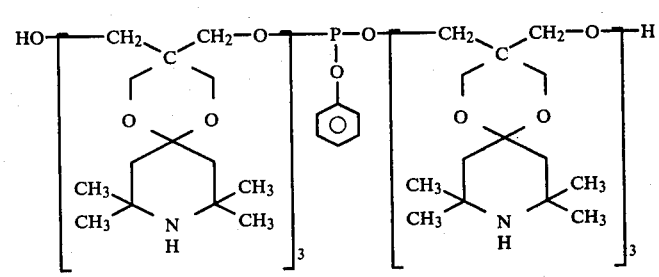
25.
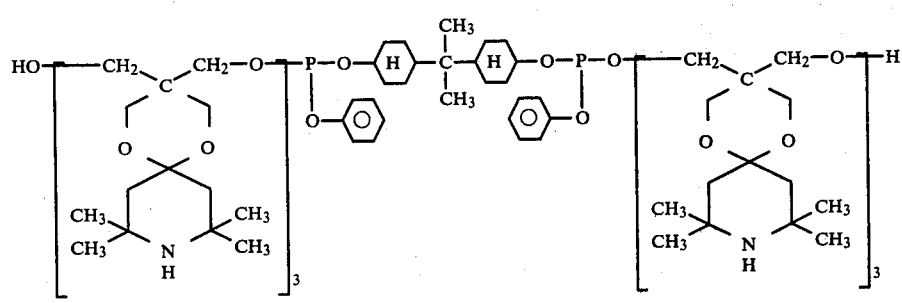
26.
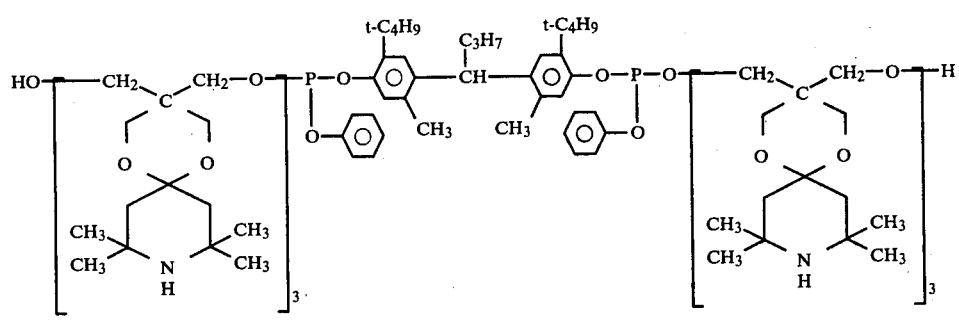
27.

-continued
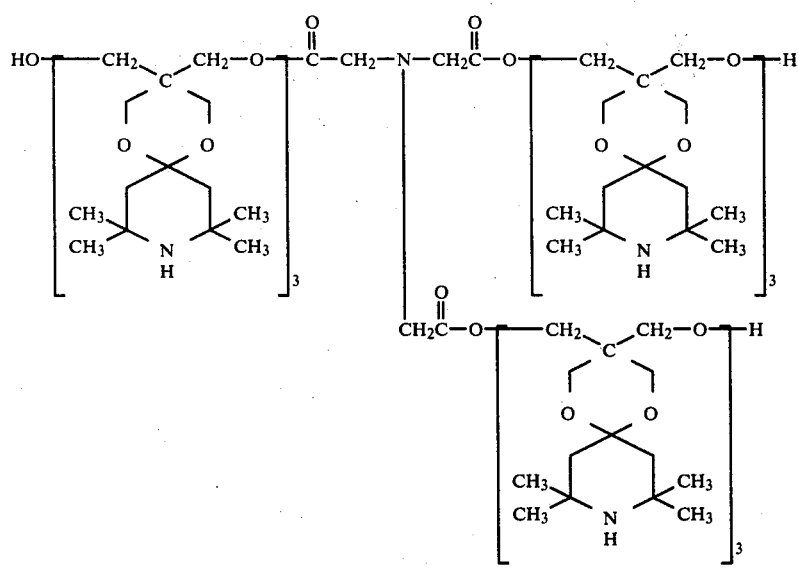
28.
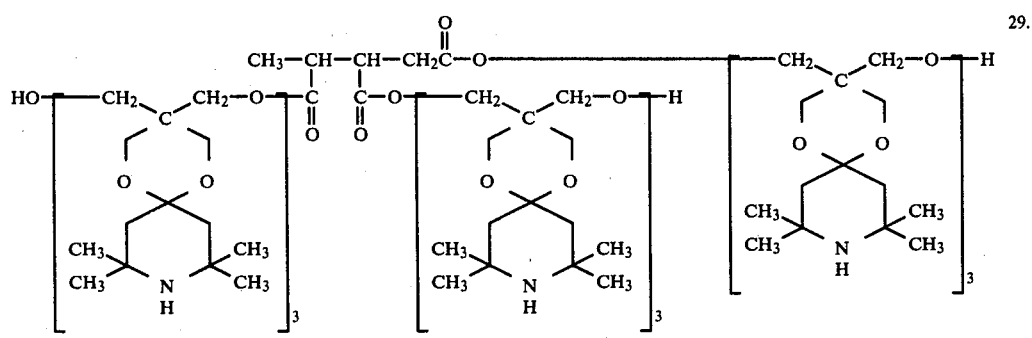
29.
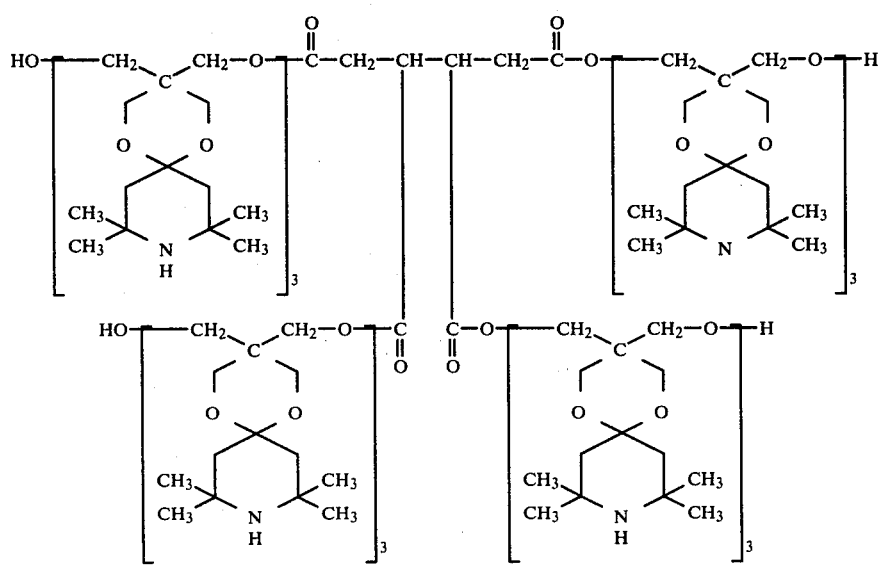
30.

-continued
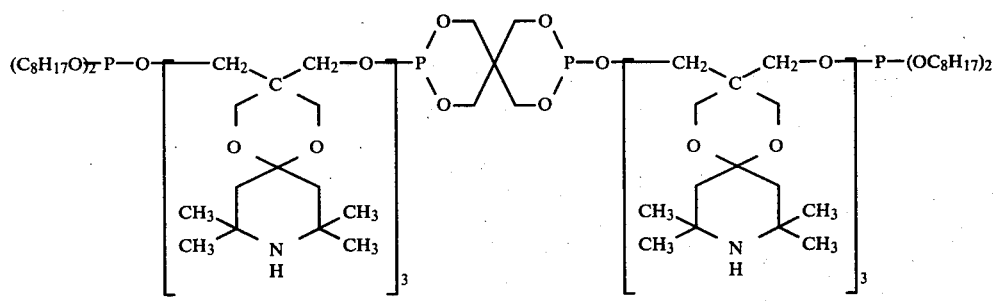 31.
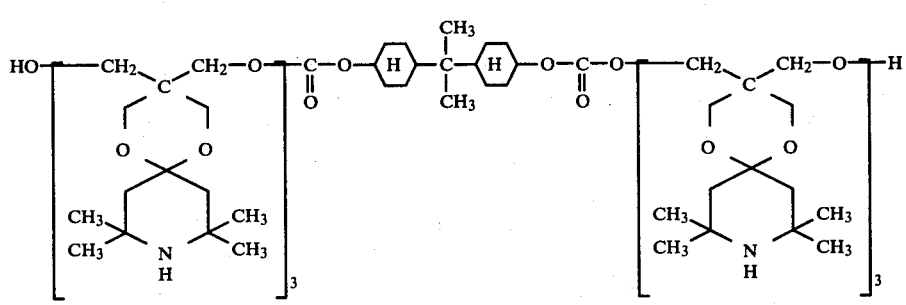 32.
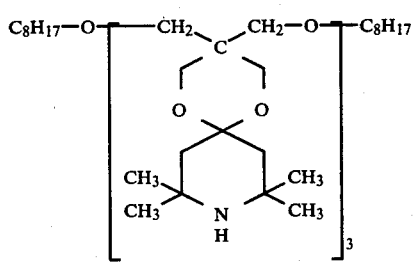 33.
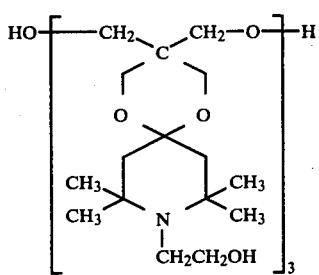 34.
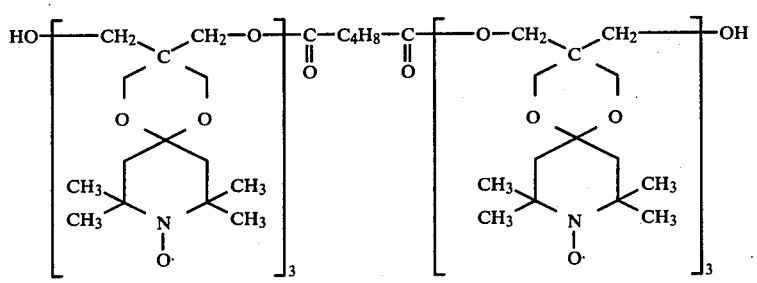 35.

-continued
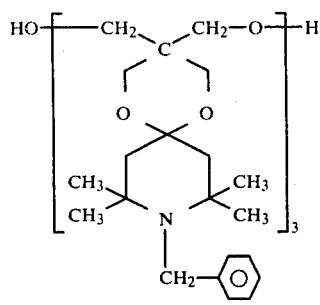 36.
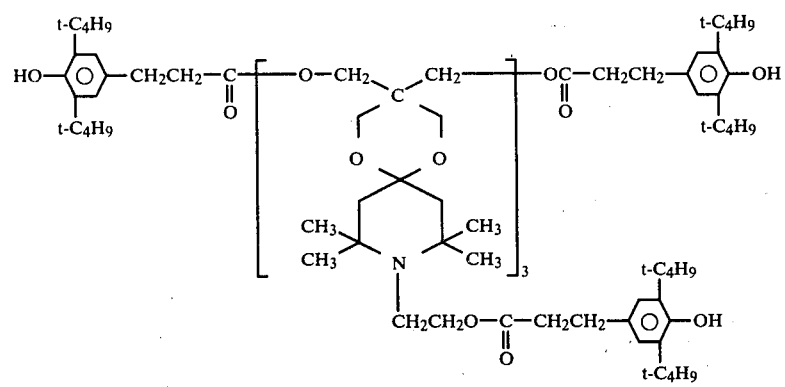 37.
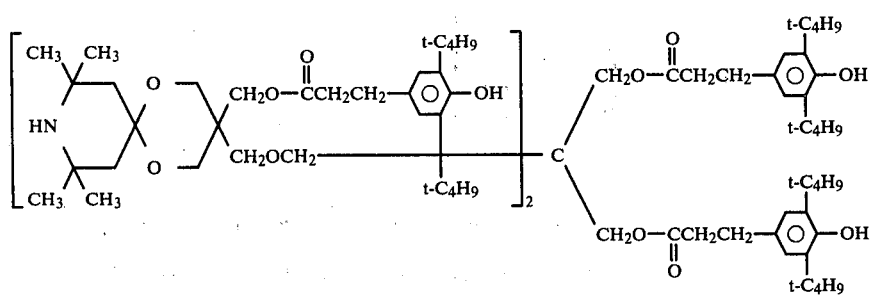 38.
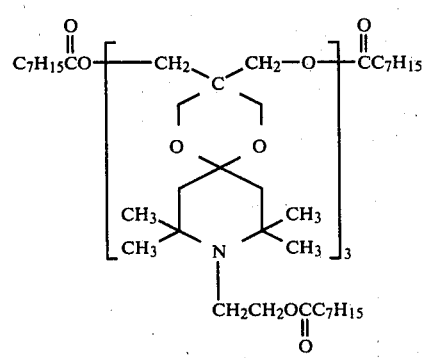 39.
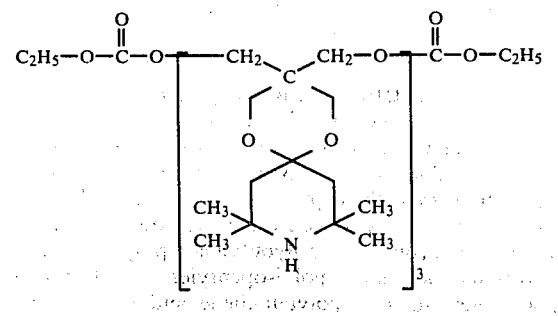 40.

-continued

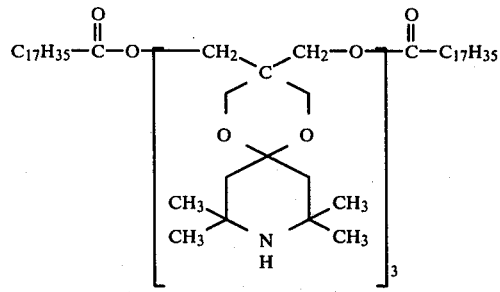
41.

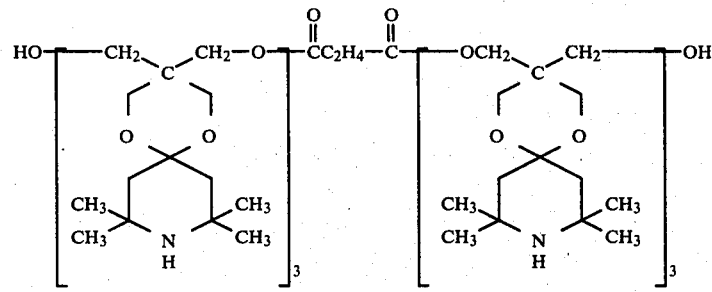
42.

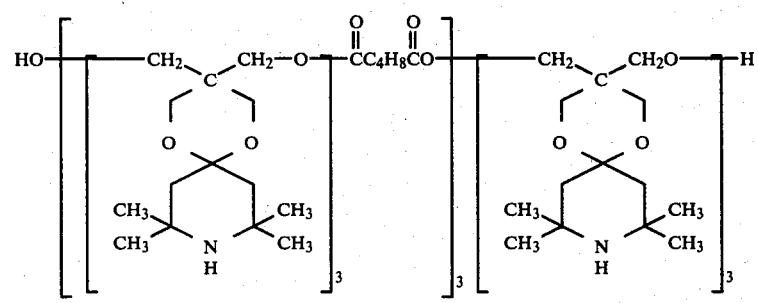
43.

EXAMPLE I

Preparation of:

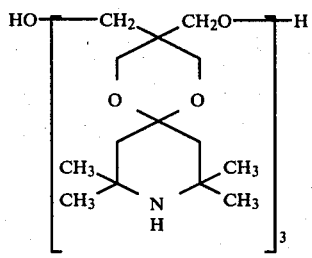

A mixture of tripentaerythritol 37.2 g (0.1 mole), 2,2,6,6-tetramethyl-4-piperidone hydrochloride 95.3 g (0.5 mole), sec-butanol 400 ml, n-hexane 50 ml and concentrated $H_2SO_4$ 1.3 g was heated under reflux for twenty-four hours while distilling off the liberated water.

After cooling, 300 g of 10% aqueous NaOH was added. The organic layer was separated, washed with water, and dried. The solvent was evaporated, and 65.2 g of white powder, m.p. 134° to 139° C. was obtained, the product of the above formula.

Compounds having the general formula (I) of this invention are readily prepared by conventional esterification or etherification of

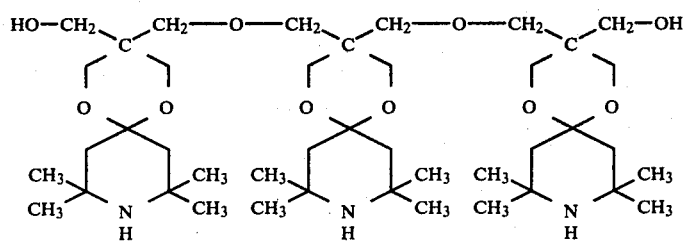

The 2,2,6,6-tetrasubstituted-4-piperidyl spiro aliphatic ethers of the invention are effective stabilizers to enhance the resistance to deterioration due to heat and/or light of synthetic polymeric materials which are susceptible to such degradation, including polyolefins such as low density polyethylene, high density polyethylene, polypropylene, polybutylene, polyisobutylene, polypentylene, and polyisopentylene; polystyrene; polydienes, such as polybutadiene and polyisoprene;

and copolymers of olefins and dienes with other ethylenically and acetylenically unsaturated monomers, such as ethylene-propylene copolymers, ethylene-butene copolymers, ethylene-pentene copolymers, ethylene-vinyl acetate copolymers, styrene-butadiene copolymers, acrylonitrile-styrene-butadiene copolymers, synthetic rubbers of all types, such as polychloroprene; polyvinyl halides, including polyvinyl chloride homopolymer; polyvinylidene chloride; and copolymers of vinyl chloride and vinylidene chloride; vinyl chloride and vinyl acetate; vinylidene chloride and vinyl acetate; and other ethylenically unsaturated monomers; polyacetals such as polyoxymethylene and polyoxyethylene; polyesters such as polyethylene glycol-terephthalic acid ester polymers; polyamides such as polyepsiloncaprolactam, polyhexamethylene adipamide and polydecamethylene adipamide; polyurethanes; and epoxy resins.

The synthetic polymer can be in any physical form, including (for example) filaments, yarns, films, sheets, molded articles, latex, and foam.

The piperidyl spiro aliphatic ethers of the invention can be used as a stabilizer in an amount within the range from about 0.001 to about 10 parts by weight, preferably from 0.01 to 5 parts by weight, per 100 parts by weight of resin.

The piperidyl siro aliphatic ethers of the invention can also be incorporated in the reaction mixture of monomers of polymerizable components used for preparation of the polymer to be stabilized, in which event the piperidyl spiro aliphatic ether can become a constituent part of the polymer molecule, and exert its stabilizing effect there. Examples are the reaction mixtures for preparation of polyaddition or polycondensation polymers such as polyurethanes and polyesters. In such cases, amounts of piperidyl spiro aliphatic ether within the range from about 0.001 to about 10 parts by weight, preferably from 0.01 to 5 parts by weight, per 100 parts by weight of total monomers or polymerizable components can be used.

The stabilizers of the invention can be employed as the sole stabilizer or, preferably, in combination with other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organic triphosphites; organotin compounds; hindered phenols; and epoxy compounds.

With polyolfin resins there can be employed fatty acid salts of polyvalent metals, organic phosphites, phenolic and thiophenolic antioxidants, and the higher fatty alcohol esters of thiodipropionic acids, such as, for example, dilauryl thiodipropionate.

With polyamide resin compositions, polyamide stabilizers such as copper salts in combination with iodides and/or phosphorus compounds and salts of divalent manganese can be used.

With synthetic rubbers and acrylonitrile-butadiene-styrene terpolymers, antioxidants such as hindered phenols and bis-phenols, polyvalent metal salts of the higher fatty acids, and organic phosphites can be used.

In addition, other conventional additives for synthetic polymers, such as plasticizers, lubricants, emulsifiers, antistatic agents, flame-proofing agents, pigments and fillers, can be employed.

The following Examples in the opinion of the inventors represent preferred embodiments of synthetic resin compositions in accordance with the invention:

EXAMPLES 1 to 12

A group of polyvinyl chloride resin compositions was prepared having the following formulation:

| Ingredient | Parts by Weight |
| --- | --- |
| Polyvinyl chloride | 100 |
| Dioctylphthalate | 48 |
| Epoxidized soybean oil | 2 |
| Tris-nonyl phenyl phosphite | 0.2 |
| Ca stearate | 1.0 |
| Zn stearate | 0.1 |
| Stabilizer as shown in Table I | 0.3 |

This formulation was blended and sheeted off on a two-roll mill to form sheets 1 mm thick. The light resistance of these sheets was then determined by placing strips 1 cm wide in a Weather-O-Meter, and exposing them to ultraviolet light. The time in hours was then noted for the sheets to develop a noticeable discoloration and/or embrittlement, indicating deterioration due to oxidation in the presence of ultraviolet light.

This test was repeated for the stabilizers in accordance with the invention, having the formulae indicated in Table I, in comparison with four controls, oxabis-(9-aza-3-ethyl-8,8,10,10-tetramethyl-1,5-dioxaspiro[5,5]-3-undecylmethane),bis-(9-aza-3-ethyl-8,8,10,10-tetramethyl-1,5-dioxaspiro[5,5]-3-undecylmethyl) carbonate, oxabis-(9-aza-3-hydroxymethyl-8,8,10,10-tetramethyl-1,5-dioxaspiro[5,5]-3-undecyl methane) and 1-(3,5-di-t-butyl-4-hydroxyphenylpropionyloxyethyl)-2,2,6,6-tetramethyl-4-piperidinyl-3,5-di-t-butyl-4-hydroxyphenylpropionate.

The following results were obtained:

TABLE I

| | Stabilizer | Hours to Failure |
| --- | --- | --- |
| Control 1 | None | 180 |
| Control 2 | Oxabis-(9-aza-3-ethyl-8,8,10,10-tetramethyl-1,5-dioxaspiro [5,5]-3-undecylmethane) | 590 |
| Control 3 | Bis-(9-aza-3-ethyl-8,8,10,10-tetramethyl-1,5-dioxaspiro [5,5]-3-undecylmethyl)carbonate | 260 |
| Control 4 | Oxabis-(9-aza-3-hydroxymethyl-8,8,10,10-tetramethyl-1,5-dioxaspiro [5,5]-3-undecyl methane) | 600 |
| Control 5 | 1-(3,5-di-t-butyl-4-hydroxyphenyl-propionyloxyethyl)-2,2,6,6-tetramethyl-4-piperidinyl-3,5-di-t-butyl-4-hydroxyphenylpropionate | 430 |
| Example No. | | |

TABLE I-continued

| | Stabilizer | Hours to Failure |
|---|---|---|
| 1 | (structure) | 890 |
| 2 | (structure) | 820 |
| 3 | (structure) | 780 |
| 4 | (structure) | 750 |
| 5 | (structure) | 850 |
| 6 | (structure) | 900 |

TABLE I-continued

| | Stabilizer | Hours to Failure |
|---|---|---|
| 7 | [structure: HO−[−CH₂−C(CH₂−O−)(CH₂−O−)(−O−)(−O−)spiro with 2,2,6,6-tetramethyl-N-ethyl-piperidine, −C(O)C₈H₁₆C(O)−O−CH₂−C(...)-CH₂−O−]₃−H] | 890 |
| 8 | [structure: similar bis-spiro piperidine linked by −OC(O)NHC₆H₁₂NHC(O)O−, N−H piperidine] | 740 |
| 9 | [structure: tris(spiropiperidine-CH₂CH₂O)borate, N−H piperidine] | 750 |
| 10 | [structure: phenyl phosphite linked bis-spiropiperidine, N−H] | 820 |
| 11 | [structure: HO−[CH₂−C(CH₂−O−)(spiro dioxa)(2,2,6,6-tetramethyl-N-(CH₂CH₂OH)-piperidine)]₃−H] | 900 |

TABLE I-continued

| Stabilizer | Hours to Failure |
|---|---|
| 12 [structure: bis-(2,2,6,6-tetramethylpiperidinyl-HN) dioxaspiro compound with pentaerythritol core bearing three CH₂O—COCH₂CH₂—(3,5-di-t-butyl-4-hydroxyphenyl) ester groups and one CH₂OCH₂ linker to the piperidinyl dioxaspiro moiety, shown as [...]₂] | 840 |

It is apparent that each of the stabilizers in accordance with the invention is far superior to the Controls.

EXAMPLES 13 to 24

Polypropylene compositions were prepared using stabilizers of the invention and of the prior art, and having the following formulation:

| Ingredient | Parts by Weight |
|---|---|
| Polypropylene | 100 |
| Stearyl β-3,5-di-tert-butyl-4-hydroxyphenyl propionate | 0.2 |
| Stabilizer as shown in Table II | 0.3 |

The compositions were thoroughly blended in a Brabender Plastograph, and then compression-molded to form sheets 0.3 mm thick. Pieces 2.5 cm² were cut off from the sheets and exposed to a high pressure mercury lamp with and without immersion in hot water at 80° C. for fifteen hours. The hours to failure were noted in comparison with four prior art stabilizers, and the results are shown in Table II.

TABLE II

| | Stabilizer | Hours to Failure Without Immersion | Hours to Failure After Immersion for 15 hours |
|---|---|---|---|
| Control 1 | Oxabis-(9-aza-3-hydroxymethyl-8,8,10,10-tetramethyl-1,5-dioxaspiro[5,5]-3-undecylmethane) | 620 | 520 |
| Control 2 | 9-Aza-3-ethyl-8,8,10,10-tetramethyl-1,5-dioxaspiro[5,5]-3-undecylmethyl-3-(3,5-di-t-butyl-4-hydroxyphenyl)propionate | 610 | 500 |
| Control 3 | Bis-(2,2,6,6-tetramethyl-4-piperidinyl) sebacate | 490 | 340 |
| Control 4 | Oxabis-(8-aza-7,7,9,9-tetramethyl-1,4-dioxaspiro[4,5]-2-decylmethane) | 605 | 515 |
| Example No. 13 | [structure: HO—CH₂—C(dioxaspiro-tetramethylpiperidinyl)—CH₂—O—CH₂—C(dioxaspiro-tetramethylpiperidinyl)—CH₂—O—CH₂—C(dioxaspiro-tetramethylpiperidinyl)—CH₂—OH] | 820 | 720 |
| 14 | [structure: HO—(3,5-di-t-butyl-4-hydroxyphenyl)—CH₂CH₂COO—[CH₂—C(dioxaspiro-2,2,6,6-tetramethylpiperidinyl)—CH₂—O—]₃—COCH₂CH₂CH₂—(3,5-di-t-butyl-4-hydroxyphenyl)—OH] | 870 | 790 |

TABLE II-continued

| | | Hours to Failure | |
|---|---|---|---|
| | Stabilizer | Without Immersion | After Immersion for 15 hours |
| 15 | (structure) | 790 | 700 |
| 16 | (structure) | 770 | 680 |
| 17 | (structure) | 800 | 710 |
| 18 | (structure) | 750 | 700 |
| 19 | | 780 | 710 |

TABLE II-continued

| Stabilizer | Hours to Failure | |
|---|---|---|
| | Without Immersion | After Immersion for 15 hours |
| 20 (structure) | 800 | 720 |
| 21 (structure) | 820 | 730 |
| 22 (structure, No. 29) | 760 | 690 |
| 23 (structure, No. 32) | 810 | 720 |

TABLE II-continued

| | Hours to Failure | |
|---|---|---|
| Stabilizer | Without Immersion | After Immersion for 15 hours |

[Structure: HO−[−CH₂−C(CH₂−O)−(O)(O)−with 2,2,6,6-tetramethylpiperidine ring N−CH₂−phenyl]₃−H]

| | 24 | 820 | 730 |

[Structure: HO−[−CH₂−C(CH₂−O)(O)(O)− 2,2,6,6-tetramethylpiperidine N−H]₃−OC−C₂H₄−CO−[−OCH₂−C(CH₂)(O)(O)− 2,2,6,6-tetramethylpiperidine N−H]₃−OH]

It is apparent that each of the stabilizers in accordance with the invention is far superior to the Controls.

EXAMPLES 25 to 36

Ethylene-vinyl acetate copolymer compositions were prepared using stabilizers of the invention and of the prior art, and having the following formulation:

| Ingredient | Parts by Weight |
|---|---|
| Ethylene-vinyl acetate copolymer | 100 |
| 2,6-di-t-butyl-p-cresol | 0.1 |
| Ca stearate | 0.1 |
| Zn stearate | 0.1 |
| Diisodecylphenyl phosphite | 0.2 |
| Stabilizer as shown in Table III | 0.2 |

The stabilizer was blended with the polymer on a two-roll mill at 130° C., and sheets 0.4 mm thick were then compression-molded at 140° C. from the resulting blend. Pieces 2.5 cm² were cut off from the sheets and exposed to ultraviolet light in a Weather-O-Meter for 500 hours. At the start and at the conclusion of the test, tensile strength of the sheet samples was determined.

The results in comparison with four controls, oxabis-(9-aza-3-hydroxymethyl-8,8,10,10-tetramethyl-1,5-dioxaspiro-[5,5]-3-undecylmethane), bis-(2,2,6,6-tetramethyl-4-piperidinyl) succinate, oxabis-(9-aza-3-ethyl-8,8,10,10-tetramethyl-1,5-dioxaspiro-[5,5]-3-undecylmethane) and condensed compound of 1-hydroxyethyl-2,2,6,6-tetramethyl-4-piperidinol with dimethyl succinate (molecular weight >2,000) are given in Table III as percent retention of the initially determined tensile strength:

TABLE III

| | Stabilizer | % Retention of Tensile Strength After 500 Hours |
|---|---|---|
| Control 1 | Oxabis-(9-aza-3-hydroxy-methyl-8,8,10,10-tetramethyl-1,5-dioxaspiro-[5,5]-3-undecylmethane) | 70 |
| Control 2 | Bis-(2,2,6,6-tetramethyl-4-piperidinyl)succinate | 62 |
| Control 3 | Oxabis-(9-aza-3-ethyl-8,8,10,10-tetramethyl-1,5-dioxaspiro[5,5]-3-undecylmethane) | 68 |
| Control 4 | Condensed compound of 1-hydroxy-ethyl-2,2,6,6-tetramethyl-4-piperidinol with dimethyl succinate (Molecular weight 2,000) | 65 |
| Exam- | | |

TABLE III-continued

| ple No. | Structure | |
|---|---|---|
| 25 | (complex chemical structure with three 2,2,6,6-tetramethylpiperidine spiro-dioxane units linked by -CH2-O-CH2- bridges, terminated by HO-CH2- groups) | 78 |
| 26 | (structure with phenyl carbonate end groups linked through -CH2-C(spiro-dioxane-piperidine)-CH2-O-C(=O)-O- repeating units, brackets subscripted 3) | 82 |
| 27 | (structure with HO-C(=O)-O- end groups and repeating units with brackets subscripted 3, middle bracket subscripted 5) | 83 |
| 28 | (structure with PhNHC(=O)O-CH2- end groups, three spiro-dioxane-N-methylpiperidine units linked by -CH2-O-CH2- bridges) | 80 |
| 29 | (structure with CH3-C(=O)-O- acetate end groups, spiro-dioxane-piperidine units with brackets subscripted 3, middle succinate -O-C(=O)-CH2CH2-C(=O)-O- with bracket subscripted 2) | 83 |

TABLE III-continued
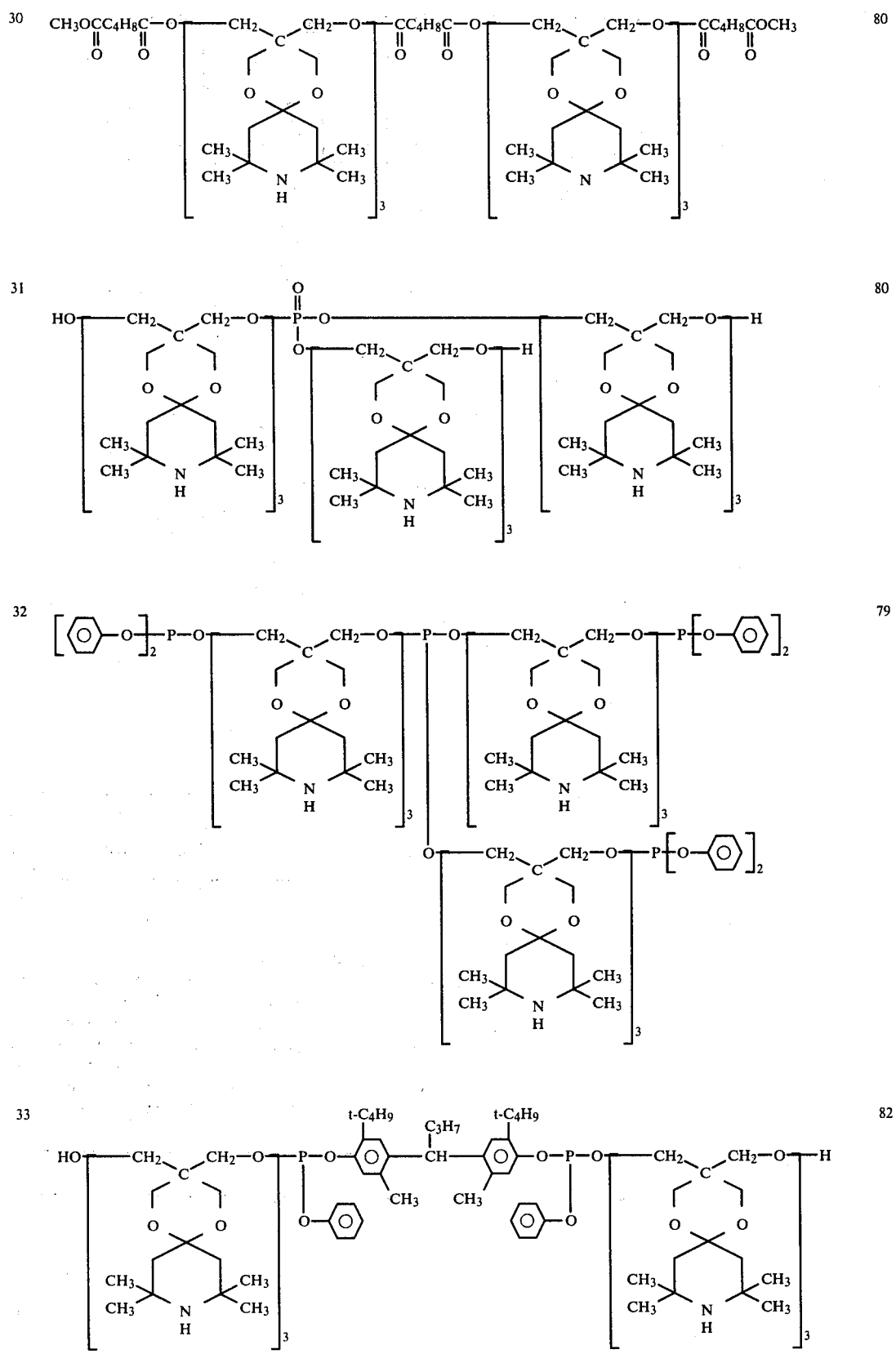

TABLE III-continued

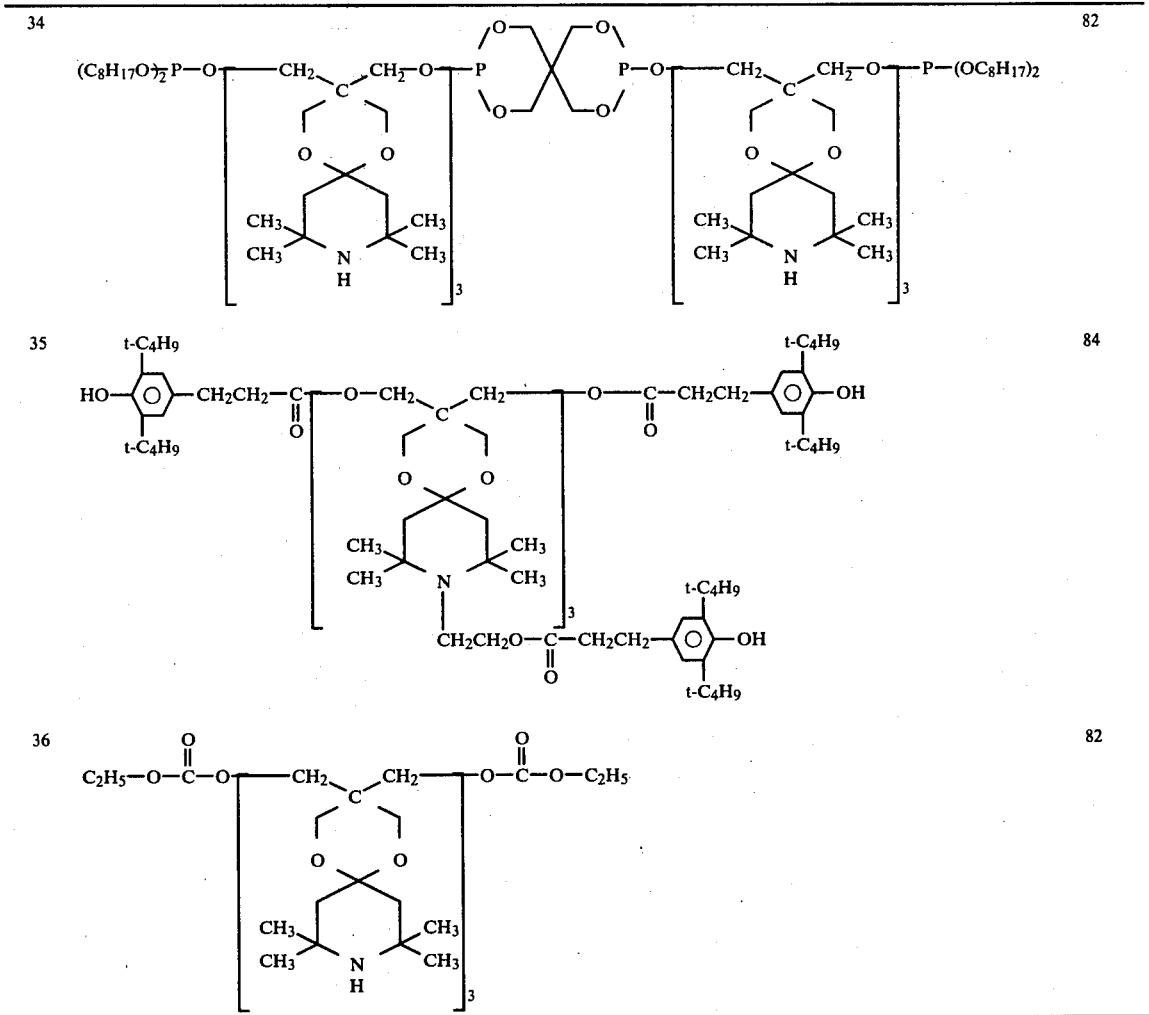

| | | |
|---|---|---|
| 34 | | 82 |
| 35 | | 84 |
| 36 | | 82 |

It is apparent that each of the stabilizers in accordance with the invention is far superior to the Controls.

EXAMPLES 37 to 48

High density polyethylene compositions were prepared using the stabilizers of the invention and of the prior art, and having the following formulation:

| Ingredient | Parts by Weight |
|---|---|
| High-density polyethylene | 100 |
| Ca stearate | 1 |
| Tetrakis-(methylene-3-(3,5-di-t-butyl-4-hydroxyphenyl)propionate)methane | 0.1 |
| Distearylthiodipropionate | 0.3 |
| Stabilizer as shown in Table IV | 0.2 |

The stabilizer was blended with the polymer on a two-roll mill and sheets 0.5 mm thick were prepared by compression-molding of the blend. Pieces 2.5 cm$^2$ were cut off from the sheets, and exposed in a Weather-O-Meter to ultraviolet light. The time in hours when degradation set in, as determined by a significant discoloration and/or embrittlement, was noted as hours to failure, and the results are reported in Table IV.

TABLE IV

| | Stabilizer | Hours to Failure |
|---|---|---|
| Control 1 | Oxabis-(9-aza-3-ethyl-8,8,10,10-tetramethyl-1,5-dioxaspiro[5,5]-3-undecylmethane) | 870 |
| Control 2 | Tris-(9-aza-3-ethyl-8,8,10,10-tetramethyl-1,5-dioxaspiro[5,5]-3-undecylmethyl)phosphite | 900 |
| Control 3 | 2,2,4,4,18,18,20,20-Octamethyl-3,19-diaza-7,15,22,26-tetraoxa-24-hydroxy tetraspiro[5,2,3,2,5,2,1,2,]-hexaeicosane | 860 |

TABLE IV-continued
| Example No. | | |
|---|---|---|
| Control 4 | Bis-(2,2,6,6-tetramethyl-4-piperidinyl)adipate | 680 |
| 37 | 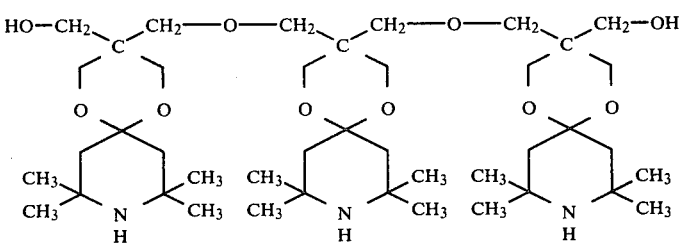 | 1220 |
| 38 | 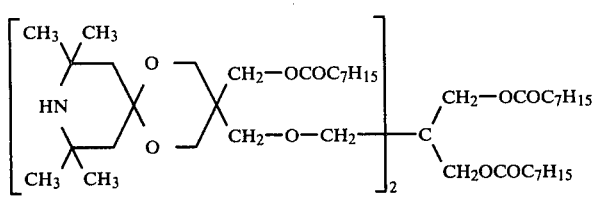 | 1180 |
| 39 | 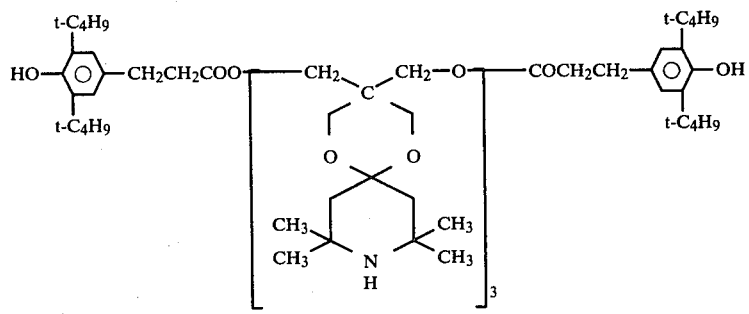 | 1310 |
| 40 | 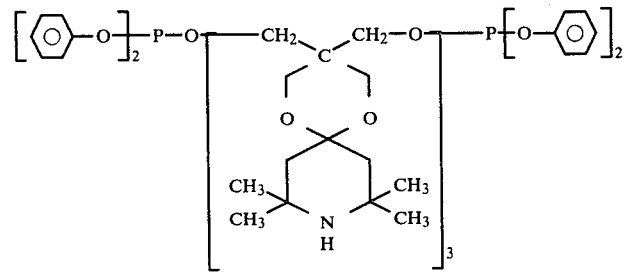 | 1200 |
| 41 | 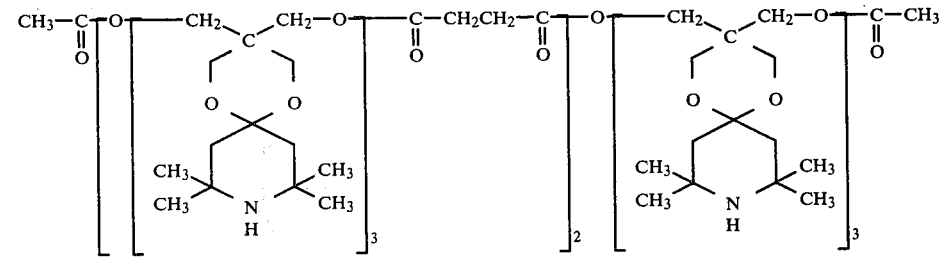 | 1280 |

TABLE IV-continued
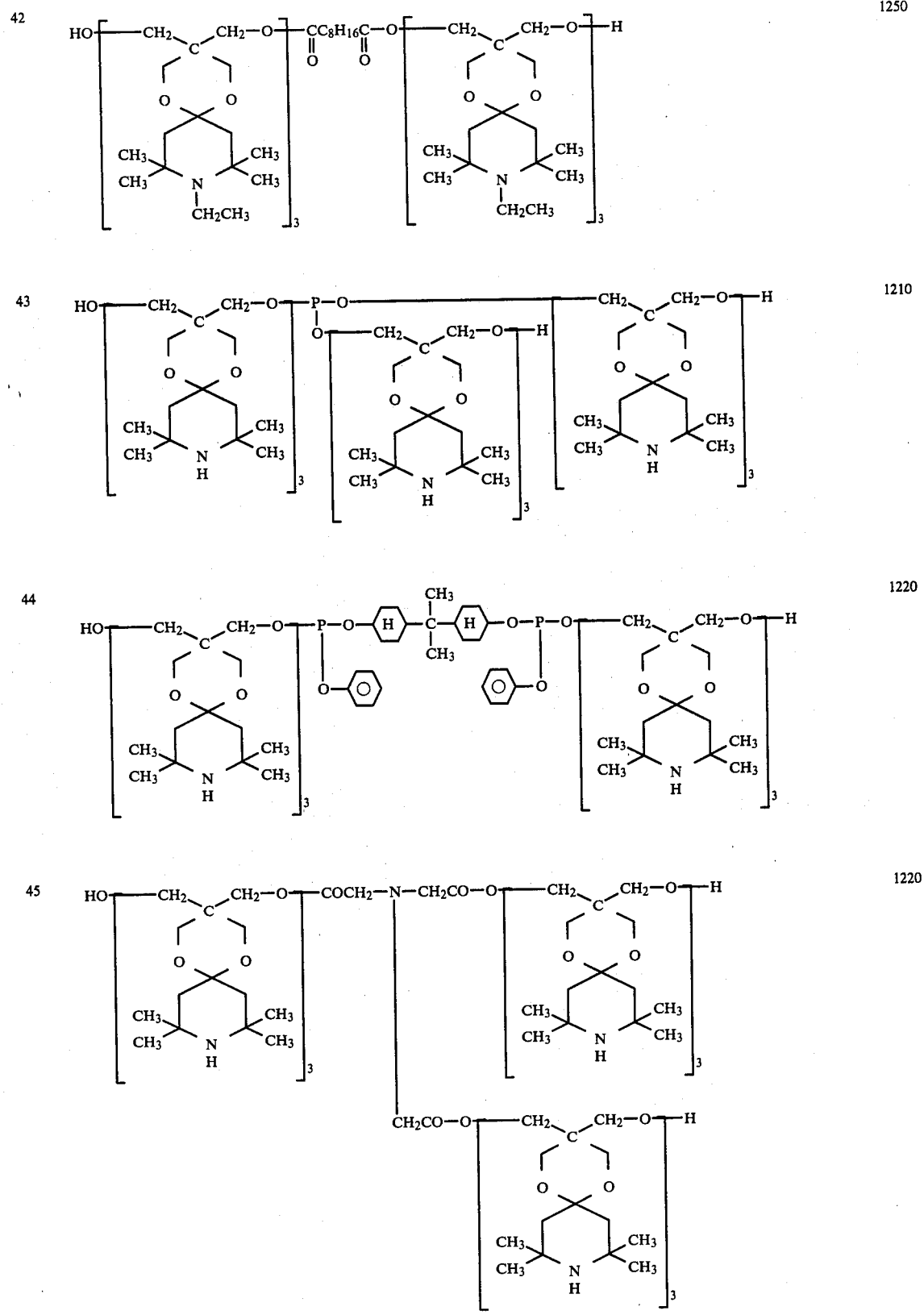

TABLE IV-continued

| # | Structure | Value |
|---|---|---|
| 46 | (structure) | 1250 |
| 47 | (structure) | 1210 |
| 48 | (structure) | 1230 |

It is apparent that each of the stabilizers in accordance with the invention is far superior to the Controls.

EXAMPLES 49 to 60

Acrylonitrile-butadiene-styrene terpolymer resin compositions were prepared using stabilizers of the invention and of the prior art, and having the following formulation:

| Ingredient | Parts by Weight |
|---|---|
| Acrylonitrile-butadiene-styrene-terpolymer | 100 |
| 4,4'-Butylidene-bis-(2-tert-butyl-m-cresol) | 0.1 |
| Stabilizer as shown in Table V | 0.3 |

The stabilizer was blended with the resin on a two-roll mill, and sheets 3 mm thick were prepared by compression-molding of the resulting blend. Pieces 2.5 cm$^2$ were cut off from the sheets, and subjected to ultraviolet light in a Weather-O-Meter for 800 hours. Tensile strength before and after the test exposure was determined, and the results reported as the percent of tensile strength retained, at the end of this time, in Table V.

TABLE V

| | Stabilizer | % Tensile Strength Retained |
|---|---|---|
| Control 1 | Oxabis-(9-aza-3-hydroxy-methyl-8,8,10,10-tetramethyl-1,5-dioxaspiro[5,5]-3-undecyl-methane) | 65 |
| Control 2 | 2(2'-Hydroxy-5'-methylphenyl)benzotriazole | 63 |
| Control 3 | Bis-(9-aza-3-ethyl-8,8,10,10-tetramethyl-1,5-dioxaspiro[5,5]-3-undecylmethyl)carbonate | 62 |
| Control 4 | 3,15-Bis-(2-hydroxyethyl)2,2,4,4,14,14,16,16-octamethyl-3,15-diaza-7,11,18,21-tetraoxatrispiro-[5,2,2,5,2,2]heneicosane | 66 |

TABLE V-continued
| Example No. | Structure | |
|---|---|---|
| 49 | 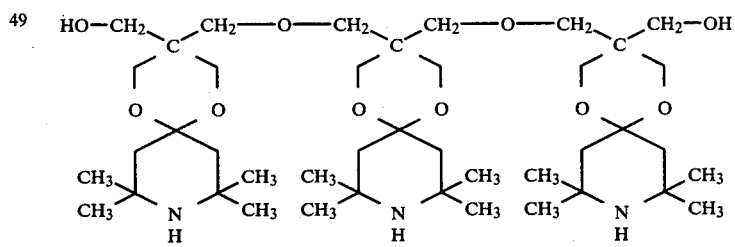 | 83 |
| 50 | 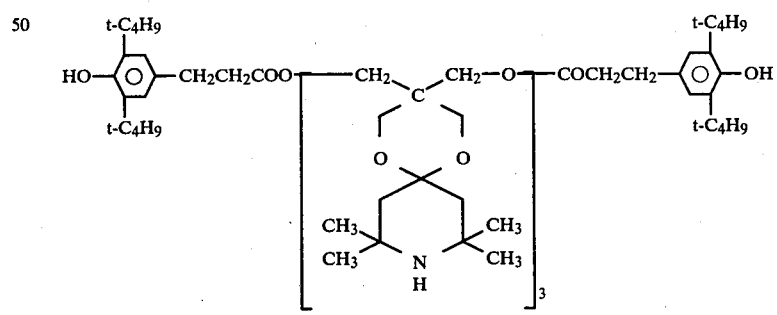 | 89 |
| 51 | 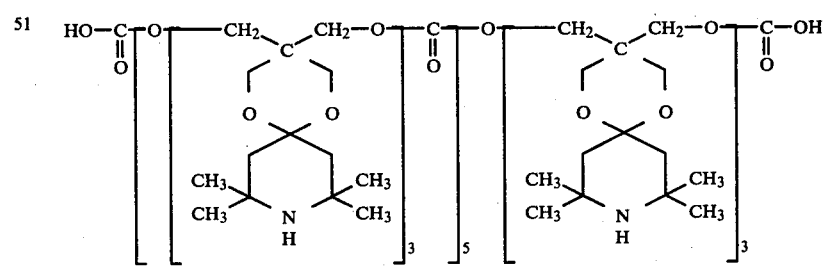 | 87 |
| 52 | 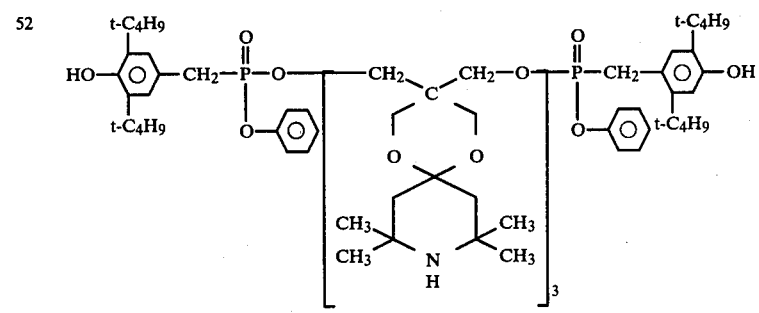 | 91 |
| 53 | 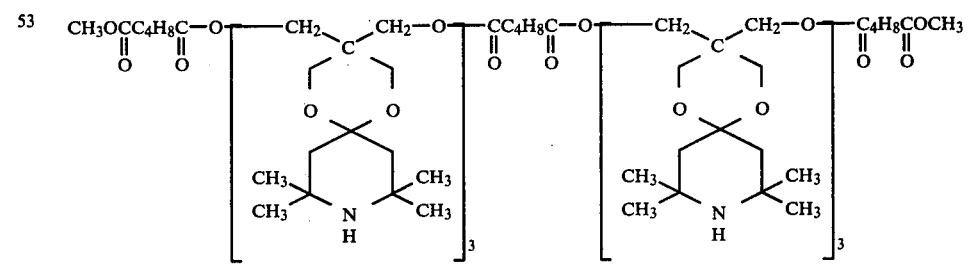 | 90 |

TABLE V-continued
54 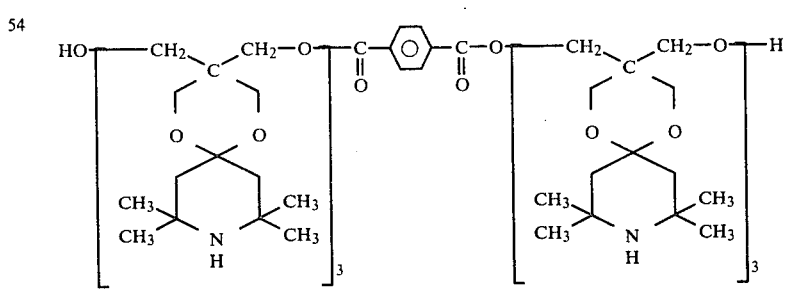 86
55 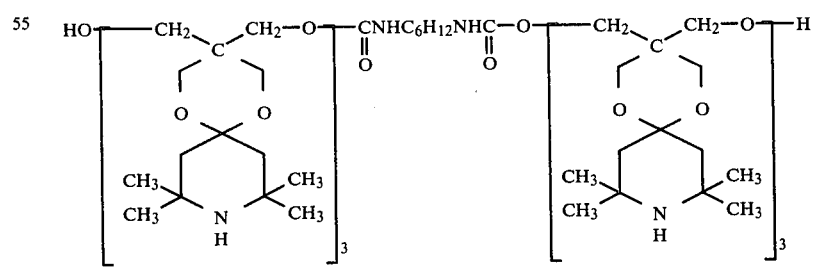 87
56 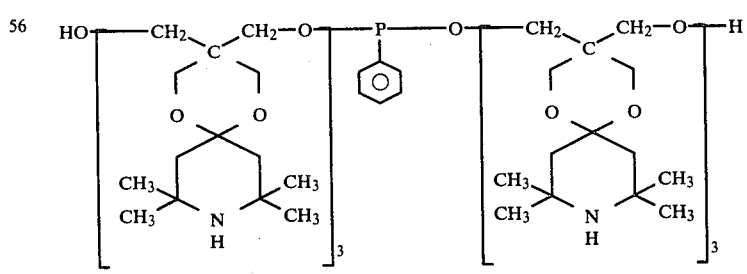 82
57 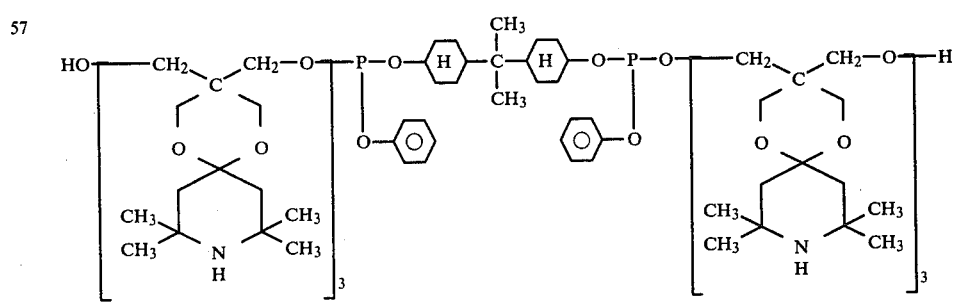 84
58 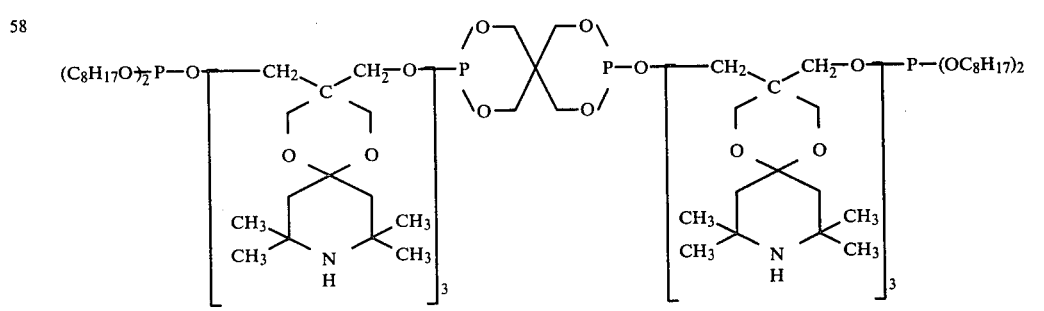 86

TABLE V-continued

| # | Structure | Value |
|---|---|---|
| 59 | HO−[−CH₂−C(CH₂−O−)−(O−)(O−) with piperidine ring having CH₃, CH₃, CH₃, CH₃ substituents and N−CH₂CH₂OH]₃ | 84 |
| 60 | HO−[−CH₂−C(CH₂−O−)−(O−)(O−) with piperidine ring having CH₃, CH₃, CH₃, CH₃ substituents and N−CH₂−C₆H₅]₃ | 82 |

It is apparent that each of the stabilizers in accordance with the invention is far superior to the Controls.

EXAMPLES 61 to 72

Conventional heat stabilizers for polymeric materials may lose their effectiveness because of volatilization or decomposition at high polymer processing temperatures. This is not true of the stabilizers of the invention, as shown by observing the effect of heat in repeated extrusions of ethylene-propylene copolymer compositions. These compositions were prepared using stabilizers of the invention and of the prior art, and having the following formulation:

| Ingredient | Parts by Weight |
|---|---|
| Ethylene-propylene copolymer | 100 |
| Ca stearate | 0.2 |
| Stearyl-β-(3,5-di-t-butyl-4-hydroxyphenyl) propionate | 0.1 |
| Dilauryl thiodipropionate | 0.2 |
| Stabilizer as shown in Table VI | 0.2 |

The ingredients were mixed and the compositions then extruded (cylinder temperature 230° C. and 240° C., head die temperature 250° C., velocity 20 rpm) five times. Test pieces were then molded by injection molding at 250° C. The test pieces were exposed to a high voltage mercury lamp, and the hours to failure noted as shown in Table VI. The surface of the test pieces was also noted after exposure for 300 hours.

TABLE VI

| | | Hours to Failure | | Surface of test pieces after exposure for 500 hours |
|---|---|---|---|---|
| | Stabilizer | Extruded 1 time | Extruded 5 times | |
| Control 1 | Bis-(9-aza-8,8,10,10-tetramethyl-3-ethyl-1,5-dioxaspiro[5,5]-3-undecylmethyl)adipate | 400 | 260 | Bloom |
| Control 2 | Bis-(9-aza-3-ethyl-8,8,10,10-tetramethyl-1,5-dioxaspiro[5,5]-3-undecylmethyl) carbonate | 380 | 250 | White spots |
| Control 3 | Oxabis-(9-aza-8,8,10,10-tetramethyl-3-hydroxymethyl-1,5-dioxaspiro[5,5]-3-undecylmethane) | 490 | 380 | White spots |
| Example No. | | | | |
| 61 | | 680 | 612 | No change |

TABLE VI-continued

| Stabilizer | Hours to Failure | | Surface of test pieces after exposure for 500 hours |
|---|---|---|---|
| | Extruded 1 time | Extruded 5 times | |
| 62 | 700 | 640 | No change |
| 63 | 710 | 660 | No change |
| 64 | 680 | 630 | No change |
| 65 | 730 | 670 | No change |
| 66 | 720 | 650 | No change |

TABLE VI-continued

| Stabilizer | Hours to Failure | | Surface of test pieces after exposure for 500 hours |
|---|---|---|---|
| | Extruded 1 time | Extruded 5 times | |
| 67 (structure shown) | 690 | 610 | No change |
| 68 (structure shown) | 710 | 630 | No change |
| 69 (structure shown) | 670 | 610 | No change |
| 70 (structure shown) | 720 | 660 | No change |

TABLE VI-continued

| | | Hours to Failure | | Surface of test pieces after exposure for 500 hours |
|---|---|---|---|---|
| | Stabilizer | Extruded 1 time | Extruded 5 times | |

71

[Structure: HO—[—CH₂—C(CH₂—O)—]₃—P—O—(aryl with t-C₄H₉, CH₃)—CH(C₃H₇)—(aryl with t-C₄H₉, CH₃)—O—P—O—[—CH₂—C(CH₂—O)—]₃—H, with spirocyclic 2,2,6,6-tetramethylpiperidine groups]

700    590    No change

72

[Structure: C₈H₁₇—O—[—CH₂—C(CH₂—O)—]₃—C₈H₁₇ with 2,2,6,6-tetramethylpiperidine spirocycle]

720    670    No change

[Structure: C₁₇H₃₅—C(=O)—O—[—CH₂—C(CH₂—O)—]₃—C(=O)—C₁₇H₃₅ with 2,2,6,6-tetramethylpiperidine spirocycle]

The results show that substantial amounts of the control stabilizers are lost by volatilization, after five extrusions, while the stabilizers of the invention are substantially retained in the polymer composition.

EXAMPLES 73 to 84

Polyurethane resin compositions were prepared using stabilizers of the invention and stabilizers of the prior art, and having the following formulation:

| Ingredient | Parts by Weight |
|---|---|
| Polyurethane resin (Asahi Denka U-100)[1] | 100 |
| Ca stearate | 0.7 |
| Zn stearate | 0.3 |
| 2,6-di-t-butyl-p-cresol | 0.1 |
| Stabilizer as shown in Table VII | 0.3 |

[1] A polyurethane-isocyanurate made from toluene diisocyanate and alkylene polyol.

The stabilizer was blended with the finely powdered polyurethane resin on a two-roll mill for five minutes at 70° C., and the sheet was then compression-molded at 120° C. for five minutes to form sheets 0.5 mm thick. Pieces 2.5 cm² were cut out from the sheets, and exposed to ultraviolet light in a Weather-O-Meter for thirty hours. Elongation before and after exposure was determined, and the percent elongation retained after the exposure is given in Table VII.

TABLE VII

| | Stabilizer | % Elongation Retention |
|---|---|---|
| Control 1 | Bis-(9-aza-3-ethyl-8,8,10,10-tetramethyl-1,5-dioxaspiro[5,5]-3-undecylmethyl) adipate | 58 |
| Control 2 | Bis-(2,2,6,6-tetramethyl-4-piperidinyl)-1,6-hexamethylene | 55 |

TABLE VII-continued
| | Stabilizer | % Elongation Retention |
|---|---|---|
| | dicarbamate | |
| Control 3 | Oxabis-(9-aza-3-hydroxymethyl-8,8,10,10-tetramethyl-1,5-dioxaspiro[5,5]-3-undecylmethane) | 64 |
| Control 4 | 9-Aza-9-(3,5-di-t-butyl-4-hydroxy-phenylpropionyloxy)ethyl-3-ethyl-8,8,10,10-tetramethyl-1,5-dioxa-spiro[5,5]-3-undecylmethyl-3,5-di-t-butyl-4-hydroxyphenylpropionate | 60 |
Example No.
73
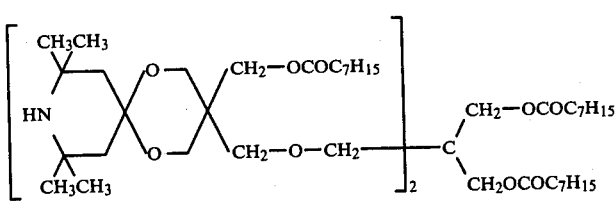
74     75
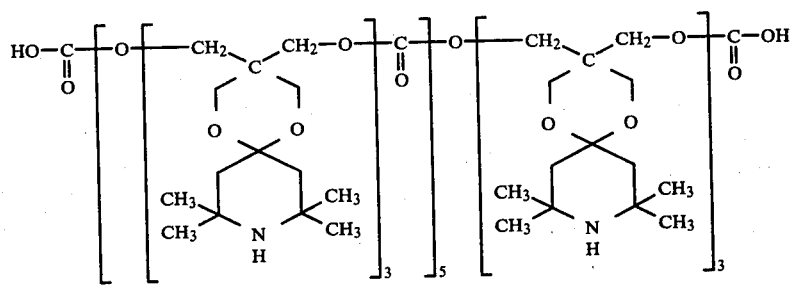
75     78
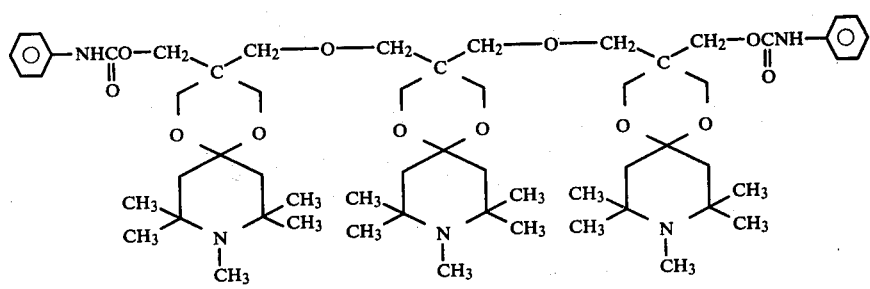
76     76
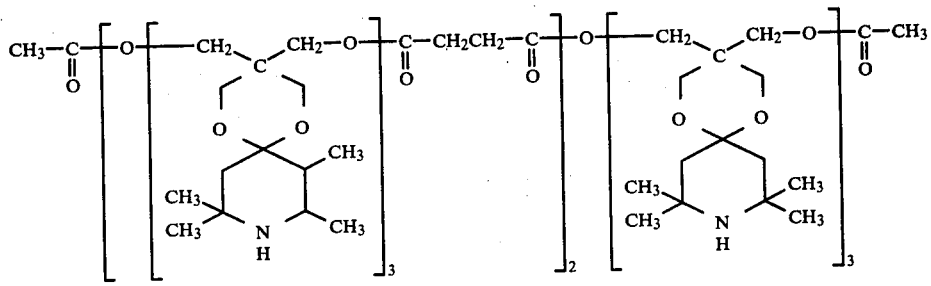
77     79

TABLE VII-continued

| Stabilizer | % Elongation Retention |
|---|---|

78: [structure] 76

79: [structure] 74

80: [structure] 72

81: [structure] 74

TABLE VII-continued
| Stabilizer | % Elongation Retention |
|---|---|
| 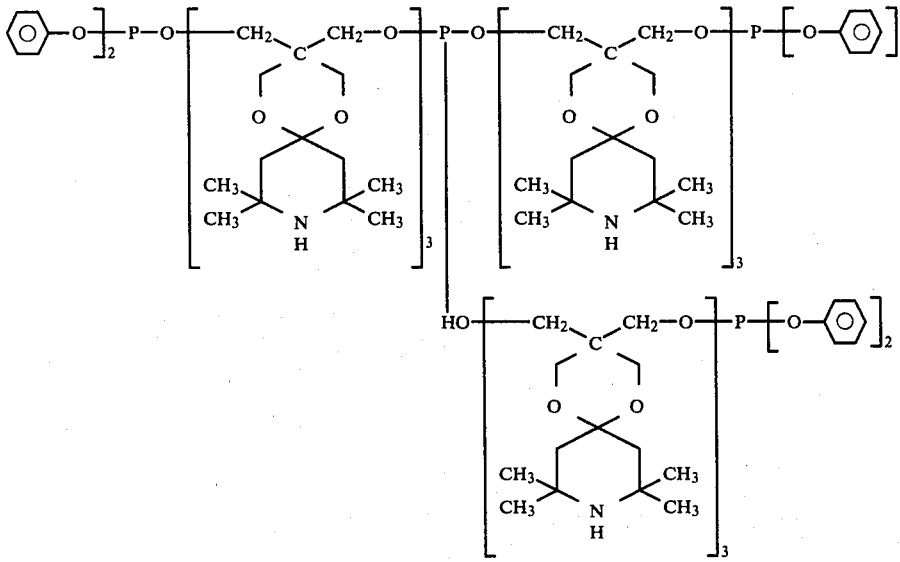 | |
| 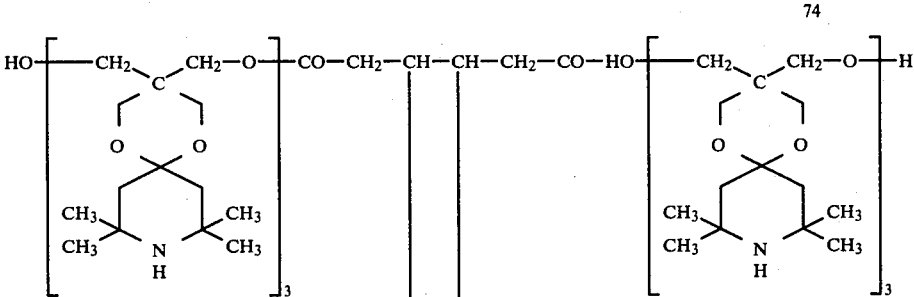 | 82 / 74 |
| 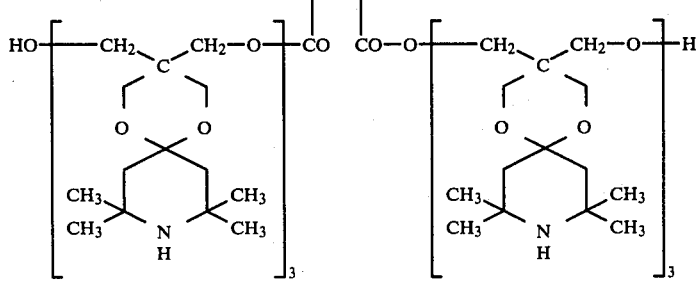 | 83 / 77 |
| 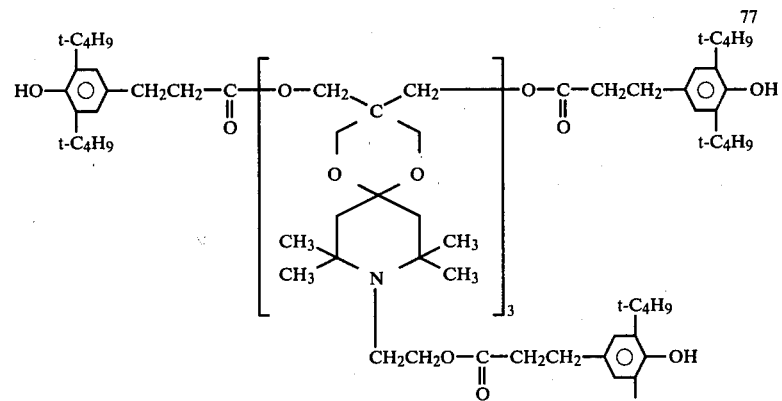 | 84 / 78 |

TABLE VII-continued

| Stabilizer | % Elongation Retention |
|---|---|
| 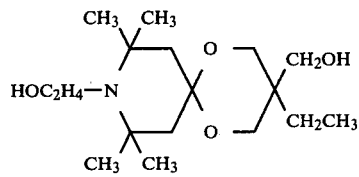 | |

The stabilizers of the invention are clearly superior to the Controls in enhancing resistance of the polyurethane resin to degradation under ultraviolet light.

The following Examples illustrate the preparation of elastomeric polyurethane fibers having some stabilizer units on the polymer backbone by using a stabilizer of the invention or prior art as a part of the monomer.

EXAMPLE 85

Preparation of elastomeric polyurethane fiber having some stabilizer units from Compound No. 1 on the polymer backbone 100.0 g (0.05 mole) of polytetramethylene ether glycol was dissolved in chlorobenzene 150 ml, and 20.0 g (0.08 mole) of diphenylmethane diisocyanate was added. The mixture was reacted for thirty minutes at 120° C. Then 2.43 g (0.027 mole) of 1,4-butylene glycol and 2.35 g (0.003 mole) of

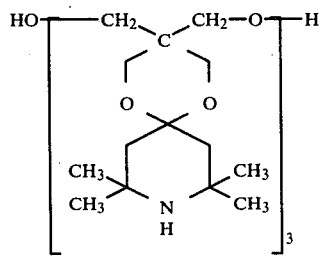

were added to the mixture, and the reaction was continued for two hours at 110° C. A 40 denier elastomeric fiber having some

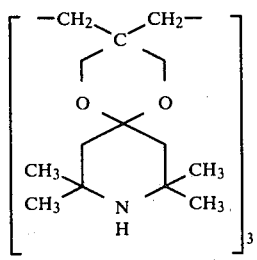

units on the polymer backbone (Sample A) was obtained from the solution by a conventional dry spinning method.

Control I

Preparation of elastomeric polyurethane fiber having stabilizer units from

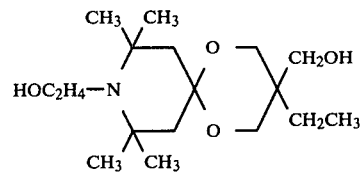

on the polymer backbone

The solution was prepared with the same formulation and under the same conditions as in Example 85, except that 1.89 g (0.02 mole) of 1,4-butylene glycol and 2.70 g (0.009 mole) of

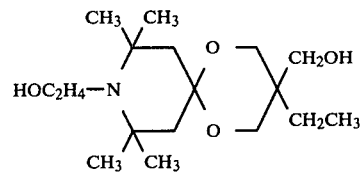

were used, in place of 2.43 g (0.027 mole) of 1,4-butylene glycol and 2.35 g (0.003 mole) of

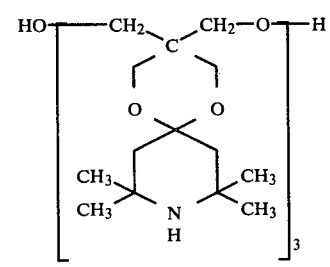

An elastomeric fiber having some

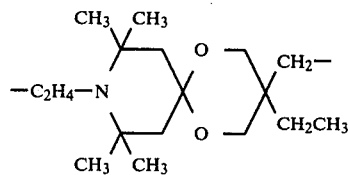

units on the polymer backbone (Sample B) was obtained from the solution.

EXAMPLE 86

Preparation of the elastomeric polyurethane fiber containing

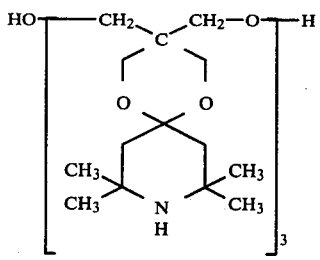

The solution was prepared with the same formulation and under the same conditions as in Example 85, except that 2.7 g (0.03 mole) of 1,4-butylene glycol in place of 2.43 g (0.027 mole) of 1,4-butylene glycol and 2.35 g (0.003 mole) of

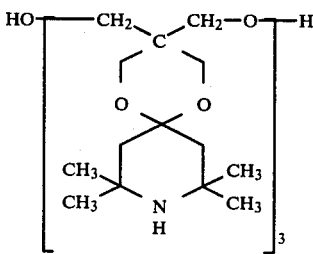

then, 2.35 g (0.003 mole) of

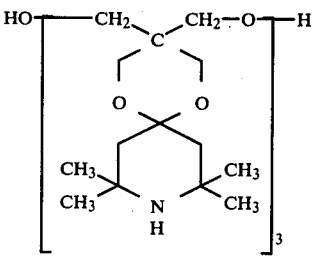

was added to the solution, and an elastomeric polyurethane fiber containing

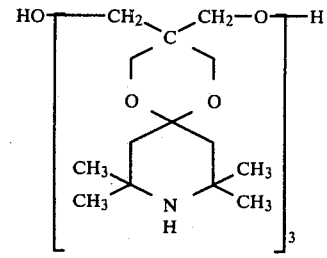

(Sample C) was obtained from the solution by a dry spinning method.

The original fibers A, B and C obtained above and fibers A, B, C after extraction with carbon tetrachloride for two hours were subjected to ultraviolet light in a Fadeometer for 72 hours. Elongation before and after the test exposure was determined, and the results reported as the percent of elongation retained, at the end of this time, in Table VIII.

TABLE VIII

| Example No. | Sample | % Elongation Retention | |
|---|---|---|---|
| | | Original Fiber | Extracted Fiber |
| Control I | B | 70 | 64 |
| Example 85 | A | 86 | 82 |
| Example 86 | C | 85 | 72 |

The fibers bonding or containing the stabilizer of the invention are clearly superior to Control I in both resistance to degradation under ultraviolet light and nonextractibility.

Having regard to the foregoing disclosure, the following is claimed as the inventive and patentable embodiments thereof:

1. 2,2,6,6-Tetramethyl-4-piperidyl spiro aliphatic ethers having the general formula:

$$R_1OY_1(\text{OXOY}_1)_{\overline{m}}OR_2 \quad\quad (I)$$
$$|$$
$$(OR_3)_p$$

wherein:
$Y_1$ is

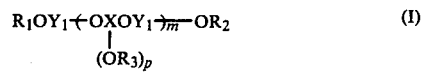

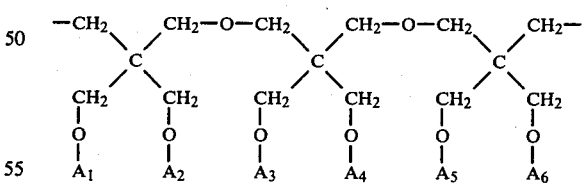

$A_1$, $A_2$, $A_3$, $A_4$, $A_5$, and $A_6$ each are selected from the group consisting of hydrogen; alkyl and hydroxyalkyl having from one to about eighteen carbon atoms; cycloalkyl having from three to about eight carbon atoms; aryl having from about six to about eighteen carbon atoms; acyl having from one to about eighteen carbon atoms

wherein R₄ is selected from the group consisting of aliphatic having from one to about eighteen carbon atoms; cycloaliphatic having from three to about eight carbon atoms; heterocyclic having from six to about eighteen carbon atoms; and aromatic having from six to about eighteen carbon atoms; carbamoyl

wherein R₅ is selected from the group consisting of aliphatic having from one to about eighteen carbon atoms; cycloaliphatic hving from three to about eight carbon atoms; heterocyclic having from six to about eighteen carbon atoms; and aromatic having from six to about eighteen carbon atoms;

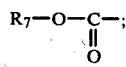

and monovalent oxyacid groups;
at least one pair of A₁ and A₂; A₃ and A₄; and A₅ and A₆ being taken together to form the group:

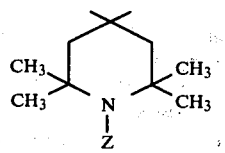

wherein:
Z is selected from the group consisting of hydrogen; oxyl O.; alkyl and hydroxyalkyl having from one to about twenty carbon atoms; and aryl and hydroxyaryl having from six to about twenty carbon atoms;
X is selected from the group consisting of alkylene having from one to about eighteen carbon atoms; cycloalkylene having from three to about eight carbon atoms; arylene having from about six to about eighteen carbon atoms; polyacyl

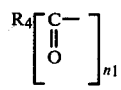

wherein R₄ is as above and n₁ is a number from 2 to 4; polycarbamoyl

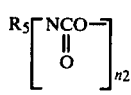

wherein R₅ is as above and n₂ is a number from 2 to 4;

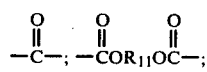

and di- and trivalent oxyacid groups;
R₁ and R₂ each are selected from the group consisting of hydrogen; alkyl having from one to about eighteen carbon atoms; cycloalkyl having from three to about eight carbon atoms; aryl having from about six to about eighteen carbon atoms; carbamoyl

wherein R₅ is selected from the group consisting of aliphatic having from one to about eighteen carbon atoms; cycloaliphatic having from three to about eight carbon atoms; heterocyclic having from six to about eighteen carbon atoms; and aromatic having from six to about eighteen carbon atoms;

and monovalent oxyacid groups;
R₃ is selected from the group consisting of alkyl having from one to about eighteen carbon atoms; cycloalkyl having from three to about eight carbon atoms; aryl having from about six to about eighteen carbon atoms; and —X—O—R₁;
R₇ is selected from the group consisting of the residues of monohydric alcohols having from one to about eighteen carbon atoms and phenols having from six to about fifty carbon atoms;
R₁₁ is selected from the group consisting of alkylene and oxyalkylene having from two to about ten carbon atoms and from zero to about five oxyether groups; cycloalkylene having from three to about eight carbon atoms; and arylene having from six to about fifty carbon atoms; and isocyanurate;
m is a number from zero to 10; and
p is zero or 1.

2. 2,2,6,6-Tetramethyl-4-piperidyl spiro aliphatic ethers according to claim 1 in which each pair of A₁ and A₂; A₃ and A₄; and A₅ and A₆ are taken together to form the group:

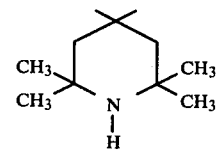

3. 2,2,6,6-Tetramethyl-4-piperidyl spiro aliphatic ethers according to claim 1 in which at least one of A₁, A₂, A₃, A₄, A₅ and A₆ is hydrogen.

4. 2,2,6,6-Tetramethyl-4-piperidyl spiro aliphatic ethers according to claim 1 in which Z is O.

5. 2,2,6,6-Tetramethyl-4-piperidyl spiro aliphatic ethers according to claim 1 in which Z is hydroxyalkyl.

6. 2,2,6,6-Tetramethyl-4-piperidyl spiro aliphatic ethers according to claim 1 in which Z is hydroxyaryl.

7. 2,2,6,6-Tetramethyl-4-piperidyl spiro aliphatic ethers according to claim 1 in which X is alkylene.

8. 2,2,6,6-Tetramethyl-4-piperidyl spiro aliphatic ethers according to claim 1 in which X is cycloalkylene.

9. 2,2,6,6-Tetramethyl-4-piperidyl spiro aliphatic ethers according to claim 1 in which X is arylene.

10. 2,2,6,6-Tetramethyl-4-piperidyl spiro aliphatic ethers according to claim 1 in which X is polyacyl

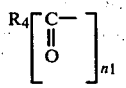

wherein $R_4$ is selected from the group consisting of aliphatic having from one to about eighteen carbon atoms; cycloaliphatic having from three to about eight carbon atoms; heterocyclic having from six to about eighteen carbon atoms; and aromatic having from six to about eighteen carbon atoms; and $n_1$ is a a number from 2 to 4.

11. 2,2,6,6-Tetramethyl-4-piperidyl spiro aliphatic ethers according to claim 1 in which X is polycarbamoyl

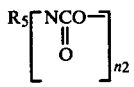

wherein $R_5$ is selected from the group consisting of aliphatic having from one to about eighteen carbon atoms; cycloaliphatic having from three to about eight carbon atoms; heterocyclic having from six to about eighteen carbon atoms; and aromatic having from six to about eighteen carbon atoms; and $n_2$ is a number from 2 to 4.

12. 2,2,6,6-Tetramethyl-4-piperidyl spiro aliphatic ethers according to claim 1 wherein X is

13. 2,2,6,6-Tetramethyl-4-piperidyl spiro aliphatic ethers according to claim 1 in which X is

14. 2,2,6,6-Tetramethyl-4-piperidyl spiro aliphatic ethers according to claim 1 in which X is a di- or trivalent oxyacid group.

15. 2,2,6,6-Tetramethyl-4-piperidyl spiro aliphatic ethers according to claim 1 wherein $R_1$ and $R_2$ each are hydrogen.

16. 2,2,6,6-Tetramethyl-4-piperidyl spiro aliphatic ethers according to claim 1 wherein $R_1$ and $R_2$ each are alkyl.

17. 2,2,6,6-Tetramethyl-4-piperidyl spiro aliphatic ethers according to claim 1 wherein $R_1$ and $R_2$ each are aryl.

18. 2,2,6,6-Tetramethyl-4-piperidyl spiro aliphatic ethers according to claim 1 wherein $R_1$ and $R_2$ each are

wherein $R_5$ is selected from the group consisting of aliphatic having from one to about eighteen carbon atoms; cycloaliphatic having from three to about eight carbon atoms; heterocyclic having from six to about eighteen carbon atoms; and aromatic having from six to about eighteen carbon atoms.

19. 2,2,6,6-Tetramethyl-4-piperidyl spiro aliphatic ethers according to claim 1 wherein $R_1$ and $R_2$ each are

wherein $R_7$ is selected from the group consisting of the residues of monohydric alcohols having from one to about eighteen carbon atoms and phenols having from six to about fifty carbon atoms.

20. 2,2,6,6-Tetramethyl-4-piperidyl spiro aliphatic ethers according to claim 1 wherein $R_1$ and $R_2$ each are monovalent oxyacid groups.

21. 2,2,6,6-Tetramethyl-4-piperidyl spiro aliphatic ethers according to claim 1 wherein m is zero.

22. 2,2,6,6-Tetramethyl-4-piperidyl spiro aliphatic ethers according to claim 1 wherein m is 1.

23. 2,2,6,6-Tetramethyl-4-piperidyl spiro aliphatic ethers according to claim 1 wherein p is zero.

24. 2,2,6,6-Tetramethyl-4-piperidyl spiro aliphatic ethers according to claim 1 wherein p is 1.

25. 2,2,6,6-Tetramethyl-4-piperidyl spiro aliphatic ethers according to claim 23 wherein $R_3$ is —X—O—$R_1$.

26. 2,2,6,6-Tetramethyl-4-piperidyl spiro aliphatic ethers according to claim 1 having the structure:

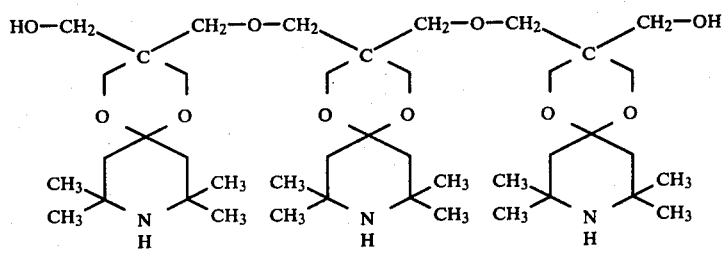

27. 2,2,6,6-Tetramethyl-4-piperidyl spiro aliphatic ethers according to claim 1 having the structure:

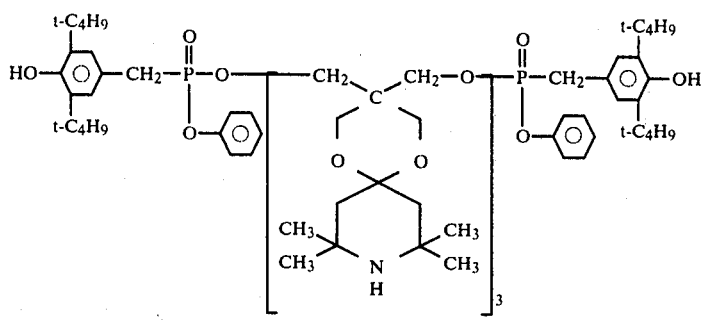
28. 2,2,6,6-Tetramethyl-4-piperidyl spiro aliphatic ethers according to claim 1 having the structure:
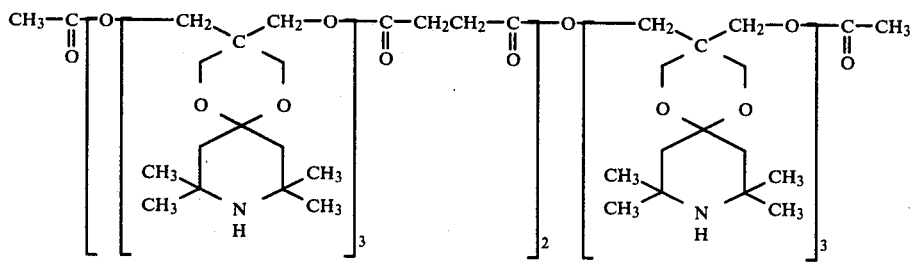
29. 2,2,6,6-Tetramethyl-4-piperidyl spiro aliphatic ethers according to claim 1 having the structure:
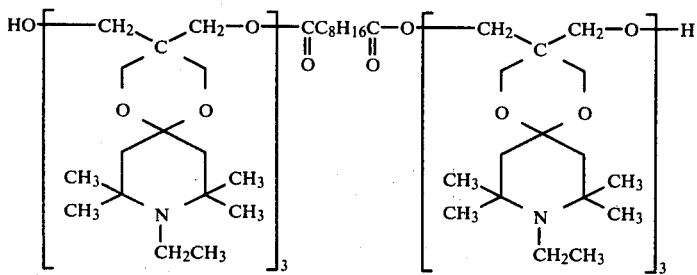
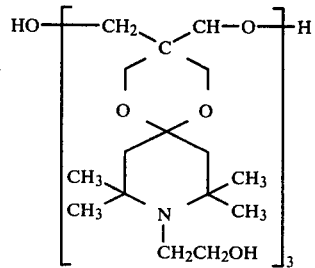
30. 2,2,6,6-Tetramethyl-4-piperidyl spiro aliphatic ethers according to claim 1 having the structure:
31. 2,2,6,6-Tetramethyl-4-piperidyl spiro aliphatic ethers according to claim 1 having the structure:

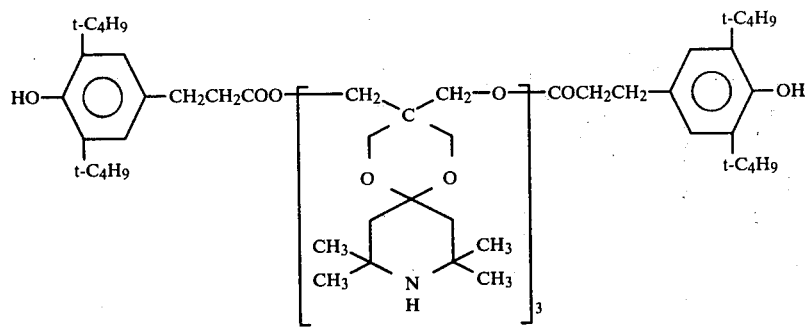

32. 2,2,6,6-Tetramethyl-4-piperidyl spiro aliphatic ethers according to claim 1 having the structure:

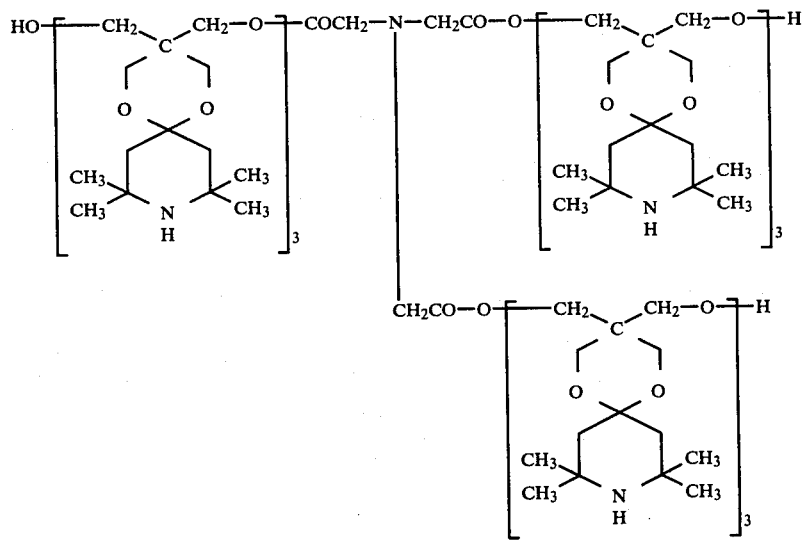

33. 2,2,6,6-Tetramethyl-4-piperidyl spiro aliphatic ethers according to claim 1 having the structure:

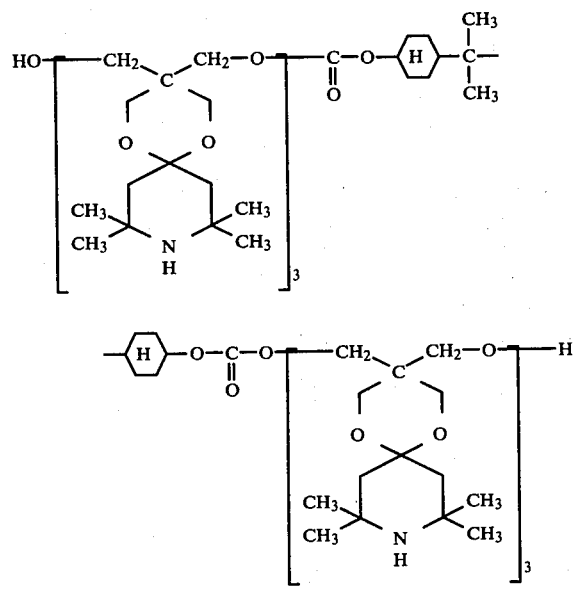

34. A polyvinyl chloride resin composition having improved resistance to deterioration when heated at 350° F., comprising a polyvinyl chloride resin formed at least in part of the recurring group

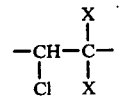

and having a chlorine content in excess of 40%, where X is either hydrogen or chlorine; and a 2,2,6,6-tetramethyl-4-piperidyl spiro aliphatic ether in accordance with claim 1.

35. A polyvinyl chloride resin composition in accordance with claim 34 in which the polyvinyl chloride resin is polyvinyl chloride homopolymer.

36. A polyvinyl chloride resin composition in accordance with claim 34 in which the polyvinyl chloride resin is a copolymer of vinyl chloride and vinyl acetate.

37. An olefin polymer composition having improved resistance to deterioration comprising an olefin polymer selected from the group consisting of polymers of alpha-olefins having from two to six carbon atoms and polystyrene, and a 2,2,6,6-tetramethyl-4-piperidyl spiro aliphatic ether in accordance with claim 1.

38. An olefin polymer composition in accordance with claim 37 wherein the polyolefin is polypropylene.

39. An olefin polymer composition in accordance with claim 37 wherein the polyolefin is polyethylene.

40. An olefin polymer composition in accordance with claim 37 wherein the polyolefin is ethylene-propylene copolymer.

41. An acrylonitrile-butadiene-styrene terpolymer having improved resistance to deterioration comprising acrylonitrile-butadiene-styrene terpolymer and a 2,2,6,6-tetramethyl-4-piperidyl spiro aliphatic ether in accordance with claim 1.

42. An ethylene-vinyl acetate copolymer composition having improved resistance to deterioration comprising ethylene-vinyl acetate copolymer and a 2,2,6,6-tetramethyl-4-piperidyl spiro aliphatic ether in accordance with claim 1.

43. A polyurethane resin composition having improved resistance to deterioration comprising a polyurethane resin and a 2,2,6,6-tetramethyl-4-piperidyl spiro aliphatic ether in accordance with claim 1.

* * * * *